US007417129B2

(12) United States Patent
West et al.

(10) Patent No.: US 7,417,129 B2
(45) Date of Patent: Aug. 26, 2008

(54) COMBINATORIAL LIBRARIES OF MONOSACCHARIDES

(75) Inventors: Michael Leo West, Queensland (AU);
Wim Meutermans, Toowong (AU);
George Adamson, Rochedale South (AU); Karl Schafer, Carina (AU);
Darren Schliebs, Burlingame, CA (US)

(73) Assignee: Alchemia Pty Ltd, Queensland (AU)

( * ) Notice: Subject to any disclaimer, the term of this patent is extended or adjusted under 35 U.S.C. 154(b) by 690 days.

(21) Appl. No.: 10/419,070

(22) Filed: Apr. 17, 2003

(65) Prior Publication Data

US 2003/0232766 A1 Dec. 18, 2003

Related U.S. Application Data

(63) Continuation-in-part of application No. PCT/AU01/01307, filed on Oct. 17, 2001.

(30) Foreign Application Priority Data

Oct. 17, 2000 (AU) .................................. PR0797

(51) Int. Cl.
*C07H 15/00* (2006.01)
(52) U.S. Cl. .................. 536/4.1; 536/16.8; 536/17.2; 536/18.2; 506/19
(58) Field of Classification Search .................. None
See application file for complete search history.

(56) References Cited

U.S. PATENT DOCUMENTS

| 4,185,089 A | 1/1980 | Derrien et al. |
| 4,866,035 A | 9/1989 | Durette .......................... 514/8 |
| 6,084,081 A | 7/2000 | Ohira et al. |

FOREIGN PATENT DOCUMENTS

| EP | 0 014 159 B1 | 7/1982 |
| EP | 0 015 468 B1 | 12/1982 |
| EP | 0 097 506 A2 | 1/1984 |
| EP | 0180961 | 5/1986 |
| FR | 2368282 | 5/1978 |
| WO | WO 9838197 | 9/1998 |
| WO | WO 01/51499 A1 | 7/2001 |

OTHER PUBLICATIONS

Zemlyakov, "Synthesis of Hydrophobic Derivatives of Muramyldipeptides" Chemistry of Natural Compounds 1997, 33(1), pp. 61-66.*
Roychoudhury et al. "Use of combinatorial library screening to identify inhibitors of a bacterial two-component signal transduction kinase" Molecular Diversity 1998, 4, 173-182.*
Buchi, J. "The Constitution-Effect Relationships from a New Viewpoint" Deutsche Apotheker-Zeitung 1966, pp. 1695-1700 (1-29 for English translation).*

Chemical Abstract 133:223029 & Liu, et al. "Solid-phase synthesis of muramyl dipeptide (MDP) derivatives using a multipin method", Bioorg. Med. Chem. Lett. 10(12):1361-1363 (2000).
Chemical Abstract 129:216855 & WO 9838197 (see above).
Chemical Abstract 123:170109 & Kuryanov et al. "Synthesis of muramyldipeptide lipophilic derivatives", Bioorg 20(4):439-477 (1994) (Russian version only; translation available upon request.).
Chemical Abstract 134:178795 & Zhang et al. "Parallel synthesis of muramyl peptides derivatives", *Peptides: Biology and Chemistry Proc. of the 5th Chinese Peptide Symposium*, 198-201, Kluwer Academic Publishers, Netherlands (2000).
Chemical Abstract 113:212524 & Hecker et al. "Synthesis of C(6) - carboxylate analogs of N-acetylmuramic acid", *J. Org. Chem.* 55(24):6051-6054 (1990).
Chemical Abstract 121:109485 & Wiemann et al. "Enzymic sythesis of N-acetyllactosamine on a soluble, light-sensitive polymer" *Carbohydr. Res.* 257(1):C1-C6 (1994).
Chemical Abstract 78:4456 & Petit et al. "Amino sugars LXXXI Synthesis of 2-amino-3-O- (L-1-carboxyethyl) -2-deoxy-D-glucose (isomuramic acid and its derivatives" *Carbohyd. Res.* 24(2):415-425 (1972).
Jeanloz, et al., "Synthesis of Various Glycosides of 2-Amino-3-O-(D-1-Carboxy-ethyl)-2-Deoxy-D-Glucopyranose (Muramic Acid)", Carbohyd. Res., 6 (1968) pp. 184-196.
Goebel, et al., "Beyond Peptide and Nucleic Acid Combinatorial Libraries-Applying Unions of Multicomponent Reactions towards the Generation of Carbohydrate Combinatorial Libraries", Tetrahedron Letters, vol. 36, No. 34, pp. 6043-6046, 1995.
Kallus, et al., "Combinatorial Solid-Phase Synthesis Using D-Galactose as a Chiral Five-Dimension-Diversity Scaffold", Tetrahedron Letters 40 (1999) pp. 7783-7786.
Sofia, et al, "Carbohydrate-Based Small-Molecule Scaffolds for the Construction of Universal Pharmacophore Mapping Libraries", J. Org. Chem. 1998, 63, pp. 2802-2803.
Silva, et al, "Stereospecific Solution- and Solid-Phase Glycosylations. Synthesis of β-Linked Saccharides and Construction of Disaccharide Libraries Using Phenylsulfenyl 2-Deoxy-2-Trifluoroacetamido Glycopyranosides as Glycosyl Donors", J. Org. Chem. 1999, 64, pp. 5926-2929.
Lohse, et al., "The First Combinatorial Library of Azasugar Glycosidase Inhibitors", Tetrahedron Letters 40 (1999) pp. 3033-3036.
Byrgesen, et al., "Combinatorial Chemistry of Piperidine Based Carbohydrate Mimics.", Tetrahedron Letters, vol. 38, No. 32, pp. 5697-5700, 1997.
Eyles, et al., "Novel ester linked glycosyl amino acids: convenient building blocks for the synthesis of glycopeptide libraries", Tetrahedron: Asymmetry 10 (1999) pp. 391-401.

(Continued)

*Primary Examiner*—Jon D Epperson
(74) *Attorney, Agent, or Firm*—Haynes and Boone LLP; Mark D. Moore

(57) ABSTRACT

A monosaccharide compound of formula I as shown in the specification. Processes for the preparation of the compound of formula I and methods of screening for antibacterial or antibiotic compounds involving the compound of formula I.

6 Claims, 5 Drawing Sheets

OTHER PUBLICATIONS

Iglesias-Guerra, et al., "Alkylating agents from sugars. Alkyl hexopyranoside derivatives as carrier systems for chlorambucil", Carbohydrate Research 316 (1999) pp. 71-84.

Vega-Perez, et al., "Alkylating Agents from Sugars. Stereoselective Synthesis of 2,3-Diaminoglucoses from Nitroalkenes, as Intermediates in the Synthesis of Carriers of Chlorambucil", Tetrahedron 55 (1999) pp. 9641-9650.

Lees, et al., "(E)-Enolbutyryl-UDP-N-acetylglucosamine as a Mechanistic Probe of UDP-N-acetylenolpyruvylglucosamine Reductase (MurB)", Biochemistry 1996, 35, pp. 1342-1351.

Gegnas, et al., "Inhibitors of the Bacterial Cell Wall Biosynthesis Enzyme Mur D", Bioorganic & Medicinal Chemistry Letters 8 (1998) pp. 1643-1648.

Tanner, et al., "Phosphinate Inhibitors of the D-Glutamic Acid-Adding Enzyme of Peptidoglycan Biosynthesis", J. Org. Chem. 1996, 61, pp. 1756-1760.

Zeng, et al., "A Phosphinate Inhibitor of the meso-Diaminopimelic Acid-Adding Enzyme (MurE) of Peptidoglycan Biosynthesis", J. Org. Chem. 1998, 63, pp. 10081-10086.

Wunberg, et al., "Carbohydrates as Multifunctional Chiral Scaffolds in Combinatorial Synthesis", Angewandte Chemie International Edition, Oct. 2, 1998, vol. 37, No. 18, pp. 2503-2505.

Park, James T., "Uridine-5'-Pyrophosphate Derivatives", I. Isolation From Staphylococcus Aureus (From the Chemical Corps Biological Laboratories, Camp Detrick, Frederick Maryland)(Received for Publication, Sep. 4, 1951), J. Biol Chem, Feb. 1952, vol. 194, No. 2, pp. 877-884.

Ha, et al., "The Kinetic Characterization of *Escherichia coli* MurG Using Synthetic Substrate Analogues", Journal of the American Chemical Society, Sep. 22, 1999, vol. 121, No. 37, pp. 8415-8426.

Szilagyi, Laszlo et al: "A carbon-13 NMR investigation of glycosyl azides and other azido sugars: stereochemical influences on the one-bond carbon-13-proton coupling constants" Carbohydrate Research , 143, 21-41 CODEN: CRBRAT; ISSN: 0008-6215, 1985, XP002444100.

McDonald, Frank E. et al: "A stereoselective route from glycals to asparagine-linked N-protected glycopeptides" Journal of Organic Chemistry , 57(26), 7001-2 CODEN: JOCEAH; ISSN: 0022-3263, 1992, XP002444101.

Unverzagt, Carlo et al: "Stereoselective synthesis of glycosides and anomeric azides of glucosamine" Journal Fuer Praktische Chemie/Chemiker-Zeitung , 334(7), 570-8 CODEN: JPCCEM; ISSN: 0941-1216, 1992, XP002444102.

Tamura, Masahiro et al: "Studies on N-glycopeptides. I. Synthesis of 2-acetimido-1-N-[N-(tert- butoxycarbonyl)-L-aspart-1-oyl-(L-phenylal anyl-L-serine methyl ester)-4-oyl]-2-deoxy-.beta.-D-copyranosylamine and analogs" Carbohydrate Research , 133(2), 207-18 CODEN: CRBRAT; ISSN: 0008-6215, 1984, XP002444103.

Zemlyakov, A. E. et al: "Synthesis of hydrophobic derivatives of muramyldipeptides" Chemistry of Natural Compounds (Translation of Khimiya Prirodnykh Soedinenii) , 33(1), 61-66 CODEN: CHNCA8; ISSN: 0009-3130, 1997 , XP002456931.

Petitou M., et al.: "Synthése des p-nitrophényl et p-aminophényl-2-acétamido-2-désoxy-beta- D- galactopyranoside" Carbohydr. Res., vol. 29, 1973, pp. 502-508, XP002456932.

Zemlyakov, A.E. et al.: "Synthesis and modification of spacered glycosides of N-acetylglucosamine" Chem. Nat. Compounds, vol. 33, 1997, pp. 563-567 , XP002456933.

Supplementary European Search Report, EP 01 97 5871, issued Oct. 30, 2007, European Patent Office, Munich.

* cited by examiner

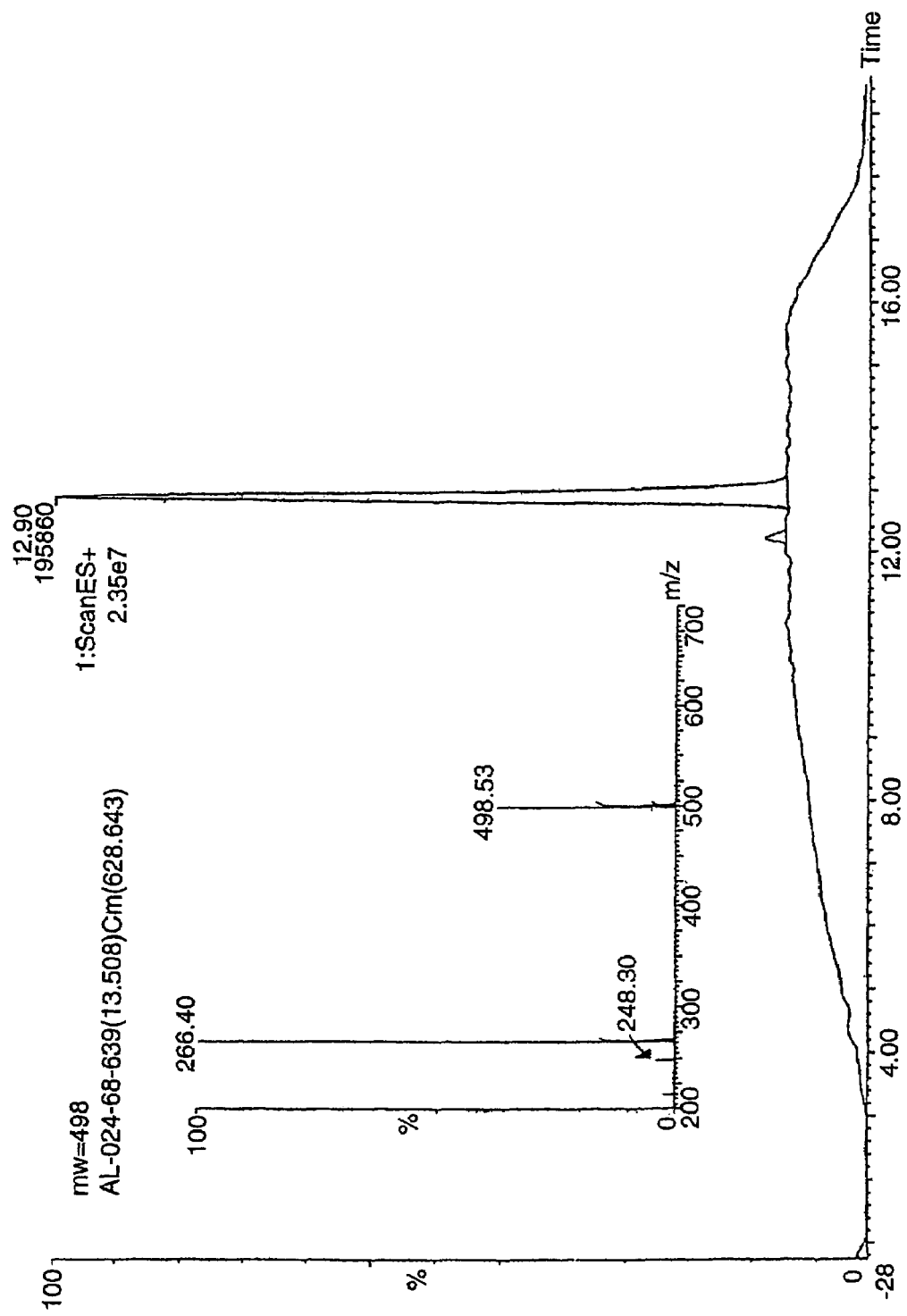
Figure 1 HPLC chromatogram and mass spectrum

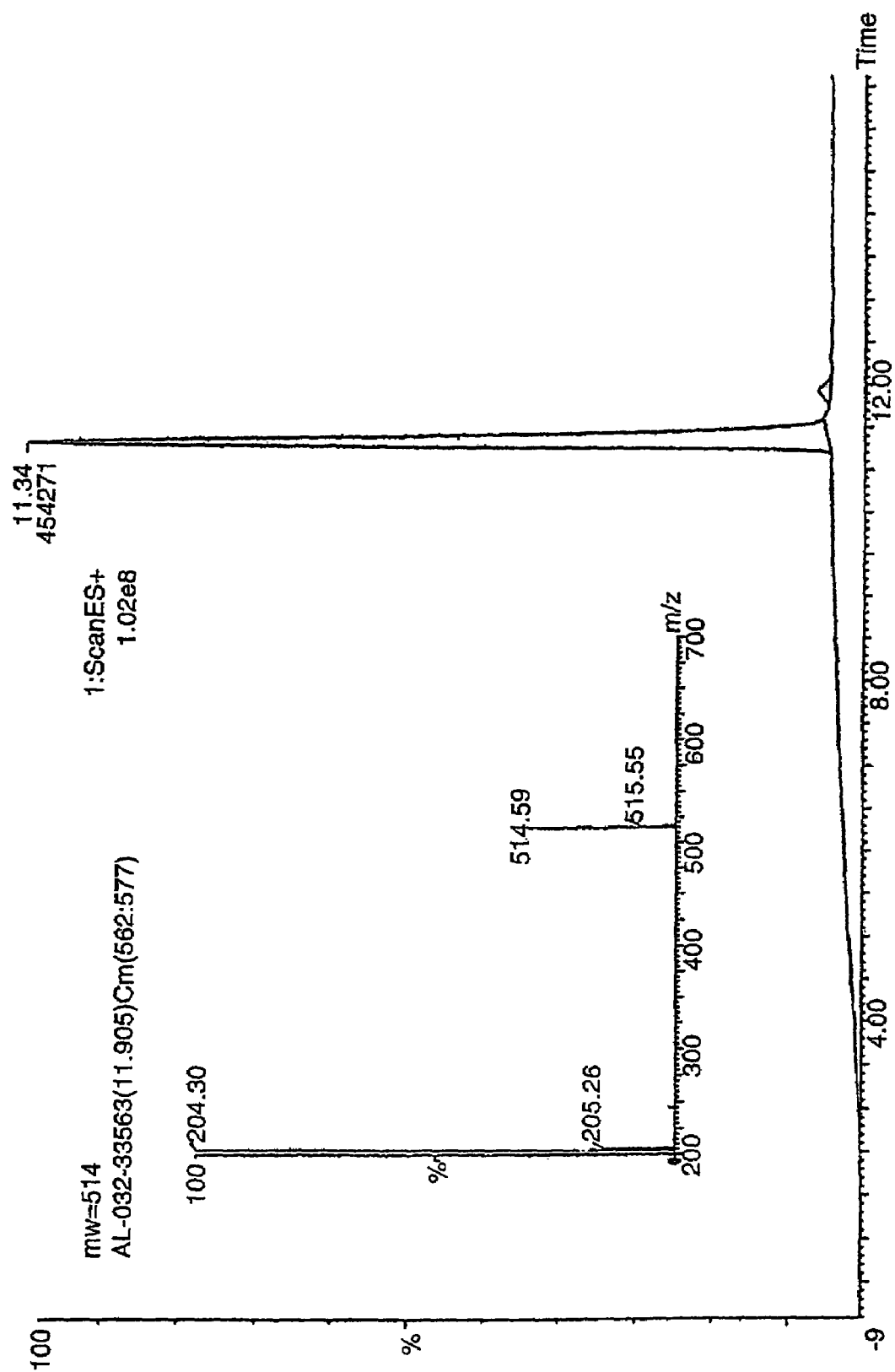
Figure 2 HPLC chromatogram and mass spectrum

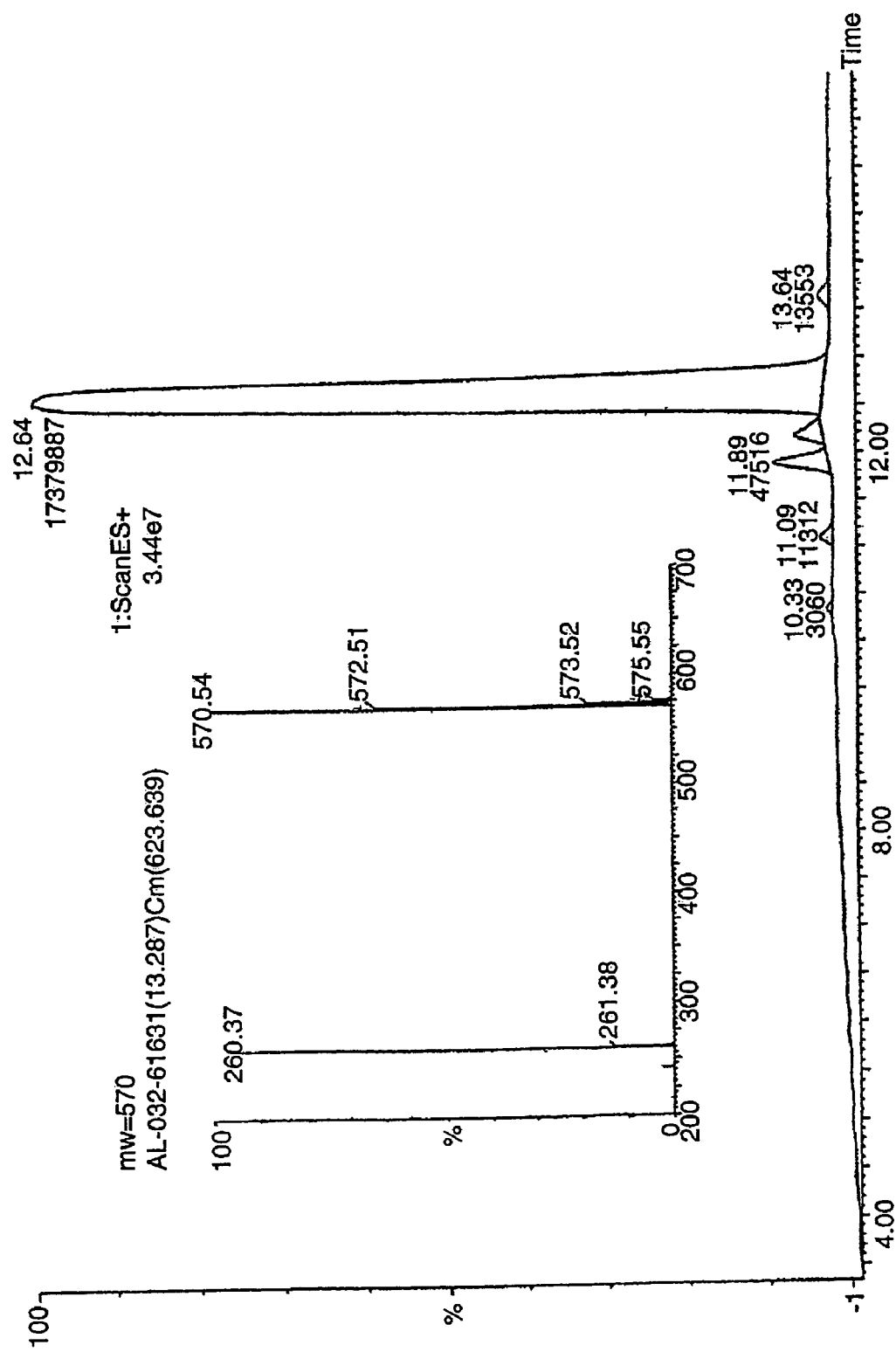
Figure 3 HPLC chromatogram and mass spectrum

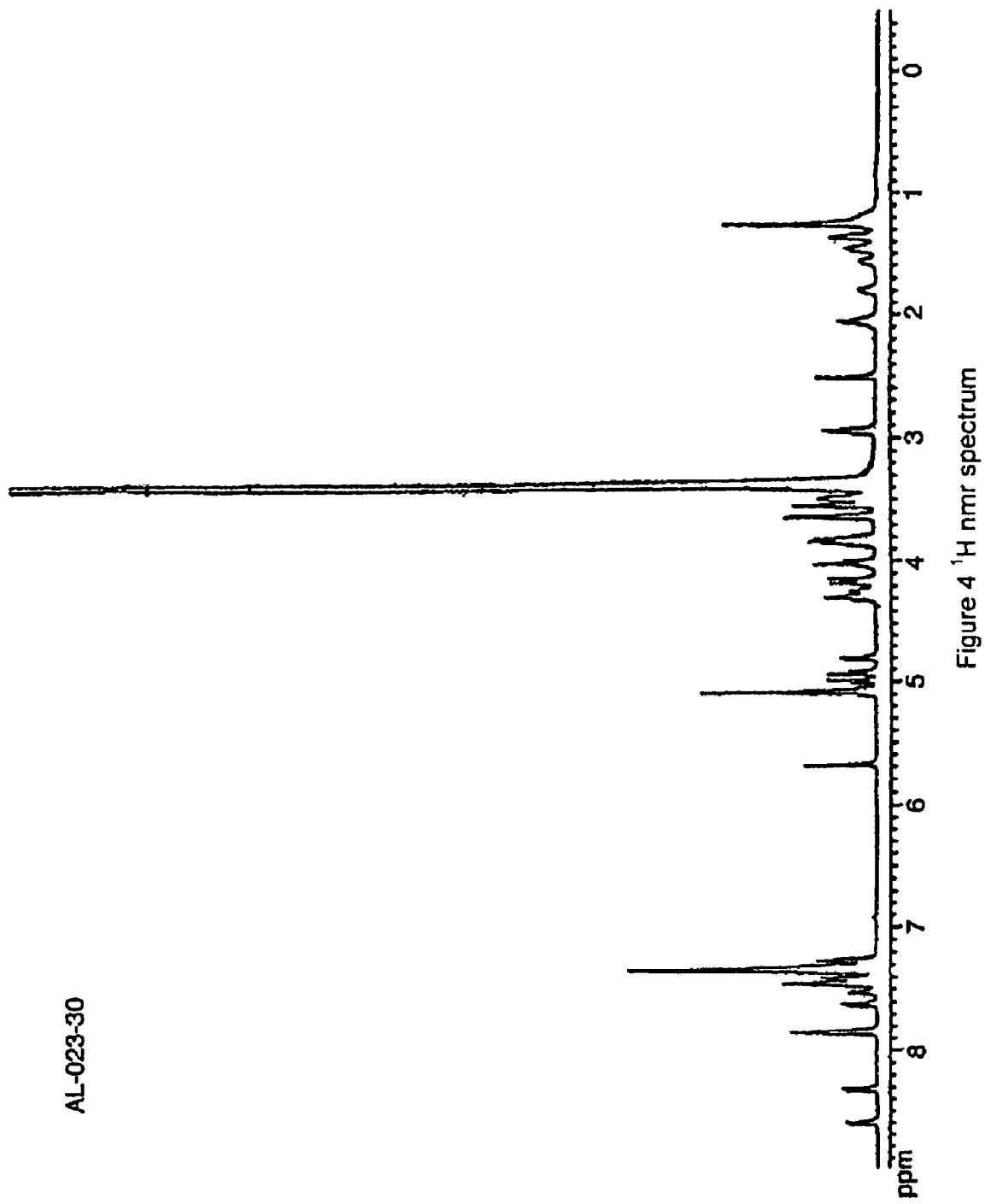
Figure 4 $^1$H nmr spectrum

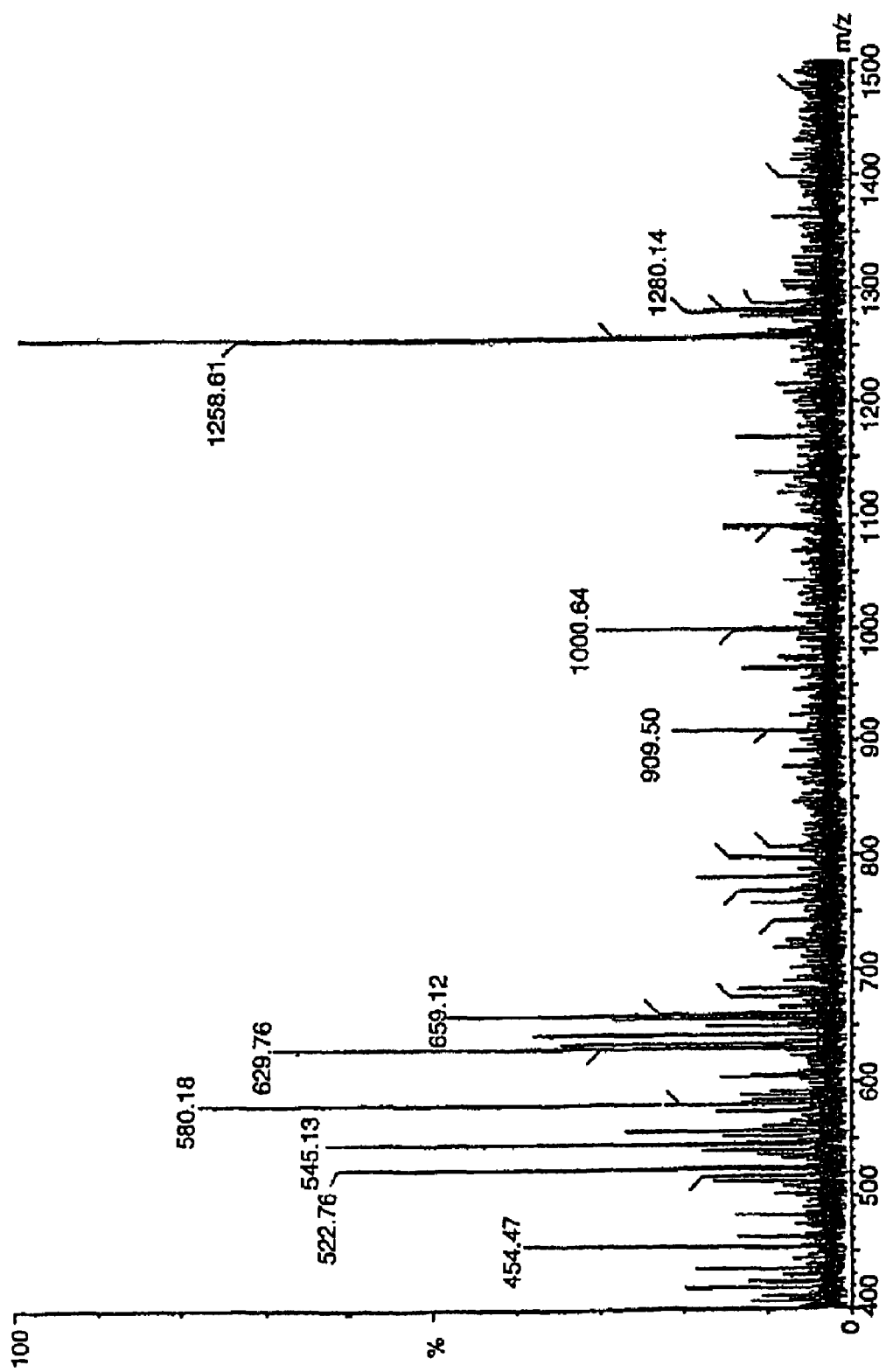
Figure 5 mass spectrum

COMBINATORIAL LIBRARIES OF MONOSACCHARIDES

CROSS-REFERENCE TO RELATED APPLICATIONS

This application is a continuation-in-part of International Application No. PCT/AU01/01307, filed Oct. 17, 2001 and designating the United States; which claims the priority of Australian Application No. PR 0797, filed Oct. 17, 2000. Each of these applications is incorporated into this application by reference.

FIELD OF THE INVENTION

This invention relates to monosaccharide compounds, methods for their preparation and their use in producing combinatorial libraries of potentially biologically active mono-or oligosaccharide compounds.

BACKGROUND OF THE INVENTION

Since the discovery of penicillin in 1928 the apparent ability of the ever-growing numbers of available antibiotics to treat infections and disease has, until recently, caused a high degree of complacency about the threat of bacterial resistance. This complacency has created a situation where antibiotics are over-prescribed in both hospitals and in the community, and used extensively in animal feeds. The alarming speed with which bacteria have become resistant to microbial agents has meant that there is a very real danger that infections, which were until recently completely controllable, will pose serious threats to human health.

All unicellular bacteria contain a cell wall which is associated with a diverse range of functions, although the major one is that of protecting the cell from lysing under high internal osmotic pressures. The cell wall is composed of peptidoglycan, a rigid mesh of β-1,4-linked carbohydrate polymers covalently cross-linked by peptide chains. The peptidoglycan synthetic pathway is not present in mammalian systems, suggesting that the side-effects associated with such inhibitors could be minimized. Thus the bacterial peptidoglycan biosynthetic pathway presents an opportunity for the development of novel antibacterial agents.

There is a great deal of interest in the substrates of the muramyl pathway and their analogues, and in the synthesis of related compounds that may result in new therapeutics. Tanner and co-workers have recently prepared compounds that inhibit the MurD and MurE enzymes of the muramyl pathway. These non-carbohydrate compounds have the sugar and lactate moieties of a muranic acid-like compound replaced with a five carbon linker unit (Zeng, B., Wong, K. K., Pompliano, D. L., , Reddy, S., and Tanner, M. E., *J. Org. Chem.* 1998, 63(26), 10081-5; Tanner, M. E., Vaganay, S., van Heijenoort,J., and Blanot, D., *J. Org. Chem.* 1996, 61(5), 1756-60), and are prepared by standard organic chemistry techniques. They are linear, flexible organic compounds with substituents that resemble those of UDP-MurNAc-pentapeptide (the "Park Nucleotide" (Park, J., *J. Biol. Chem.* 1952, 194, 877)). One of those compounds in particular was found to be a relatively potent inhibitor of MurE (Zeng, B., Wong, K. K., Pompliano, D. L., Reddy, S., and Tanner, M. E., *J. Org. Chem.* 1998, 63(26), 10081-5).

In other studies on an analogous phosphinate inhibitor of MurD, it was found that retaining the MurNAc sugar residue, instead of replacing it with a carbon linker unit, increases the potency of the inhibitor by almost two orders of magnitude (Gegnas, L. D., Waddell, S. T., Chabin, R. M., Reddy, S., Wong, K. K., *Bioorg. Med. Chem. Lett.* 1998, 8, 1643). This suggests that building a library of monosacchatide analogues of the substrates of the muramyl pathway is an attractive proposition for the generation of new therapeutics which target that system.

One approach to the synthesis of such compounds is to make use of biosynthetic techniques, such as that used in preparing labeled versions or analogues of MurNAc from GlcNAc by implementing the MurA and MurB enzymes themselves (Lees, W. J., Benson, T. E., Hogle, J. M., and. Walsh, C. T., *Biochemisty* 1996, 35(5), 1342-1351).

Chemical methods require protected building blocks, and some well-established chemistry has been implemented, using GlcNAc to yield the benzyl glycoside of N-acetyl-4,6-benzylidenemuramic acid (Jeanloz, R. W., Walker, E., Sinaÿ, P., *Carbohydr. Res.* 1968, 6, 184). One challenge to the synthesis of such compounds is the alkylation of the C-3 position of the carbohydrate residue. In the natural muramyl system, the MurA and MurB enzymes add what is ultimately a lactate moiety to the C-3 position.

The addition of a lactate moiety at C-3 has been achieved chemically in a process in which the required materials were generated through the intermediate preparation of a nitroalkene sugar (Vega-Perez, et al., *Tetrahedron* 1999, 55, 9641-9650). An alternative approach is the alkylation of the C-3 hydroxyl with the α-bromide of an appropriately protected propanoic acid to generate the required compound (Iglesias-Guerra, F., Candela, J. I., Bautista, J., Alcudia, F., and Vega-Perez, J. M., *Carbobydr. Res.* 1999, 316, 71-84).

Having compounds with a lactate moiety, or similar acid, in place at C-3 allowed the addition of amino acids to build the required pentapeptide substituent. This molecule was subsequently converted to the natural substrates for the muramyl enzyme system (Hitchcock, C. N., Eid, J. A., Aikins, M. Z-E., and Blaszczak, L. C., *J. Am. Chem. Soc.* 1998, 120(8), 1916). In a similar approach the preformed pentapeptide was added as a single unit to yield muramyl products (Ha, S., Chang, E., Lo, M-C., Men, H., Park, P., Ge, M., and Walker, S., *J. Am. Chem. Soc.* 1999, 121(37), 8415).

Combinatorial chemistry and parallel synthesis have become the methods of choice for the rapid synthesis of a large number of related compounds simultaneously, and this approach has been used to produce libraries of compounds to be screened for biological activity. Sometimes such libraries are focused to test for activity of the compounds so generated towards a particular biological agent or organism, although often large libraries are also prepared in a random fashion. Either way, the intended end result of combinatorial chemistry is the rapid discovery and optimization of leads for the development of new pharmaceuticals.

Despite the obvious advantages of a combinatorial approach to the preparation of compounds for drug discovery, this technique is underexplored in the field of carbohydrate chemistry. This is primarily because of the well-known difficulties associated with the synthesis of carbohydrate compounds. For that reason carbohydrate libraries prepared in the past have tended to be relatively simple. For example, Hindsgaul et al have produced a library of monosaccharide compounds by a combinatorial approach (Ole Hindsgaul, U.S. Pat. No. 5,780,603); however, the variation in the compounds was limited to the glycosidic bond. A glycopeptide library in which mannose residues were decorated with various amino acids has been described, but these were conjugated to the sugar solely through the C-6 position (Tennant-Eyles, R. J., and Fairbanks, A. J., *Tetrahedron Asymmetry* 1999, 10, 391-401).

Access to greater variation has been attempted by making used of libraries of carbohydrate numetics (Byrgesen, E., Nielsen, J., Willert, M., and Bols, M., *Tetrahedron Lett.* 1997, 38, 5697-5700 and Lohse, A., Jensen, K. B., and Bols, M., *Tetrahedron Lett.*, 1999, 40, 3033-3036). However, one approach which successfully added greater diversity to monosaccharides was that of Goebel and Ugi (*Tetrahedron Lett.*, 1995, 36(34), 6043-6046) who generated a small library of alkylated glycals by subjecting protected glucals to electrophilic attack and then subsequent reactions. Unfortunately this method is limited by the fact that each starting glucal may give rise to a number of isomeric products.

For these reasons there is particular interest in libraries of aminoglycosides and amino sugars for drug discovery. Some work on such compounds has been published, with Silva and co-workers preparing impressive disaccharide libraries containing glucosamine (Silva, D. J., Wang, H., Allanson, N. M., Jain, R. K., and Sofia, M. J., *J. Org. Chem.* 1999, 64(16), 5926-5929). However, this library still suffers from the limitation that the variation is limited solely to acylations of the amino group.

More variation, and in fact a three-dimensional diversity, was obtained in the preparation of amino sugars by Sofia and co-workers (Sofia, M. J., Hunter, R., Chan, T. Y., Vaughan, A., Dulina, R., Wang, H., and Gange, D., *J. Org. Chem.* 1998, 63(9), 2802-2803). This allowed chemical diversity at three combinatorial sites on the sugar residue. Other workers have prepared a library of compounds with four (Wunberg, T., Kallus, C., Opatz, T., Henke, S., Schmidt, W., and Kunz, H., *Angew. Chem. Int. Ed.* 1998, 37(18), 2503-2505), and five (Kallus, C., Opatz, T., Wunberg, T., Schmidt, W., Henke, S., and Kunz, H., *Tetrahedron Lett.* 1999, 40, 7783-7786) such sites of functionalization, although these compounds were not amino-sugars.

It will be clearly understood that, although a number of prior art publications are referred to herein, this reference does not constitute an admission that any of these documents forms part of the common general knowledge in the art, in Australia or in any other country.

Hitherto, there have been few attempts to synthesize analogues of the muramyl substrates, particularly those which contain modifications at the anomeric position or at the C-2 nitrogen. The natural substrate and all of the muramyl enzyme intermediates contain exclusively the α-glycosidic diphosphate. Our modeling and design studies with the crystal structure of the MurD enzyme suggest that both the α or β anomeric configuration of many of the compounds proposed in this invention can fit into the active site of this enzyme. We believe that this is the first time that β-glycosides which contain no phosphate groups have been prepared as potential inhibitors of the muramyl enzyme system.

Many of the traditional methods of carbohydrate synthesis have proved to be unsuitable to a combinatorial approach, particularly because modern high-throughput synthetic systems require that procedures to be readily automatable.

The documents cited throughout this application are incorporated into this application by reference.

SUMMARY OF THE INVENTION

According to the present invention there is provided a monosaccharide compound of formula I:

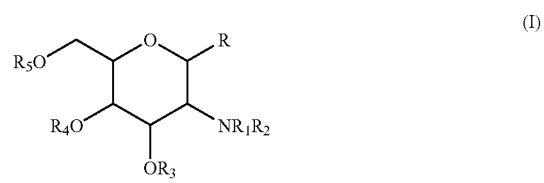

in which the monosaccharide ring substitution is of the glucosamine or galactosamine configuration and the anomerac center is either the α or β configuration;

$R_4$ and $R_5$ are hydrogen or together form an optionally substituted benzylidene acetal in which the optional substituent is chosen from halo, azido, alkoxy, nitro or alkyl;

$R_3$ is hydrogen; an optionally substituted glycolate, lactate, or derivatives thereof; or a carboxylic acid mitmetic;

R is $N_3$, O—Y,

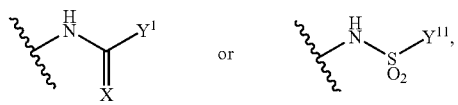

in which Y is

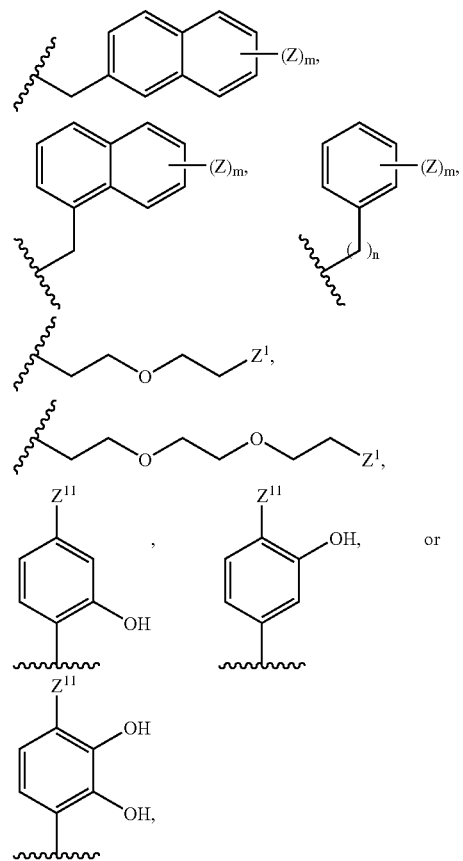

in which Z is positioned on one or both of the aromatic rings of the bicyclic structures and is independently selected from OH, SH, CF$_3$, alkyl alkenyl, alkynyl, NO$_2$, halo, SO$_3$H, NH$_2$, CO$_2$H, azido, nitroso, alkoxy, SO$_2$NH$_2$, amidine and guanidinium;

n is 0 or 1 m is an integer from 0 to 3 inclusive;

$Z^1$ is selected from halo, optionally substituted S-aryl, optionally substituted S-heteroaryl, optionally substituted aryl or optionally substituted heteroaryl;

$Z^{11}$ is selected from optionally substituted aryl, optionally substituted arylalkyl, optionally substituted heteroaryl or optionally substituted heteroarylalkyl;

X is selected from O, NH or S;

$Y^1$ is selected from

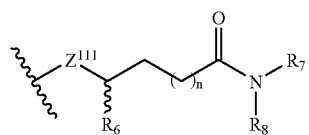

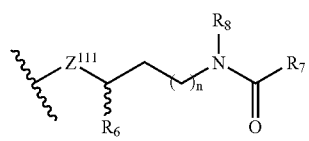

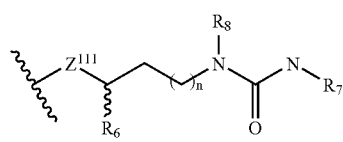

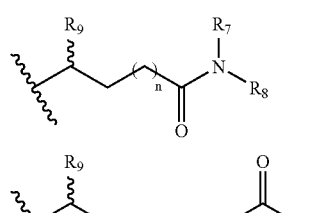

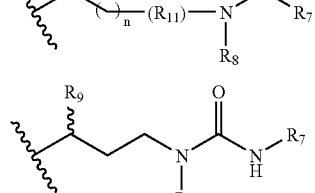

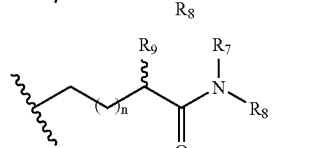

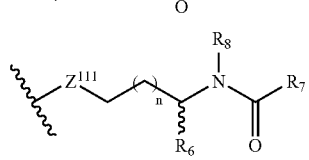

-continued

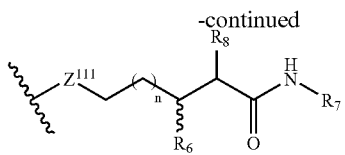

in which $Z^{111}$ is selected from O, NH or S, $R_6$ is selected from H, CONH$_2$ or COOH;

n is an integer of 0 to 4;

$R_7$ is selected from optionally substituted aryl, optionally substituted heteroaryl, optionally substituted arylalkyl or optionally substituted heteroarylalkyl $R_8$ is selected from H, OH, NH$_2$, alkyl, alkenyl or alrknyl;

$R_9$ is selected from H, OH, NH$_2$, or NHCOR$_{10}$ in which R$_{10}$ is an optionally substituted alkyl;

$R_{11}$ is selected from an optionally substituted alkylene, optionally substituted cycloalkyl, optionally substituted heterocycle, optionally substituted aryl or optionally substituted heteroaryl; and $Y^1$ or $Y^{11}$ is selected from optionally substituted aryl, optionally substituted heteroaryl, optionally substituted alkyl, optionally substituted arylalkyl or optionally substituted heteroaryl alkyl, derivatives thereof, tautomers thereof and/or isomers thereof;

with the provisos that:

(i) when R is N$_3$ or O—Y in which Y is

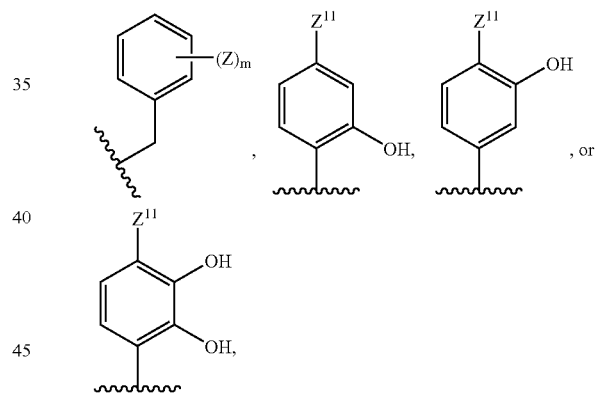

and m is 0, then $R_1$ is selected from a substituted acetyl, an optionally substituted C$_{3-8}$ acyl, an optionally substituted benzoyl, an optionally substituted naphthyl, an optionally substituted biphenylcarbonyl, a heteroaryl acyl, an optionally substituted bicycloacyl, an optionally substituted bicycloheteroacyl a sulfonamide, a urea or a carbamate; and $R_2$ is hydrogen; or $R_1$ and $R_2$ together form a succinimide, maleimide or a substituted phthalimide; and (ii) when R is O—Y,

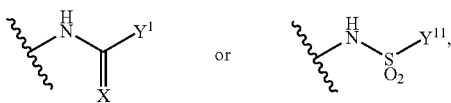

in which Y is

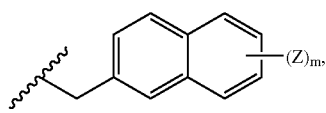

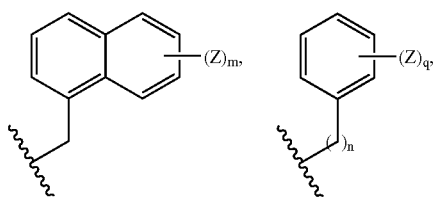

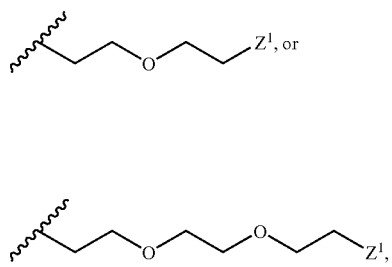

and q is an integer from 1 to 3 inclusive, then
R$_1$ is selected from an optionally substituted acetyl, an optionally substituted C$_{3-8}$ acyl, an optionally substituted benzoyl, an optionally substituted naphthyl, an optionally substituted biphenylcarbonyl, a heteroaryl acyl an optionally substituted bicycloacyl, an optionally substituted bicycloheteroacyl, a sulfonamide, a urea or a carbamate; and
R$_2$ is hydrogen; or
R$_1$ and R$_2$ together form a succinimide, maleimide or a substituted phthalimide.

The compounds of the invention are variously functionalized, with a view to varying lipid solubility, size, function and other properties, with the particular aim of the discovery of novel drug or drug-like compounds, or compounds with useful properties. The invention provides intermediates, processes and synthetic strategies for the solution or solid phase synthesis of various amides of α- and β-D-glucosarrine and -galactosamine, their PEG-glycosides and other glycosides, with various functionality about the sugar ring, including the addition of aromaticity, and the placement of amino acid and peptide units or their isosteres.

These compounds are structural mimetics of the substrates of enzymes in the muramyl pathway in peptidoglycan biosynthesis. It is expected that compounds of the type proposed, or analogues thereof, will act as inhibitors of the formation of the peptidoglycan layers that protect bacterial cell membranes or as inhibitors of other bacterial enzymes. Thus compounds of this type are attractive targets for the discovery of new antibiotics and antibacterials.

Thus the compounds and methods disclosed herein provide the ability to produce random or focused combinatorial-type libraries not only for the discovery of new antibacterial agents, but also for the discovery of other novel drug or drug-like compounds, or compounds with other useful properties.

A preferred compound of formula I has the formula Ia

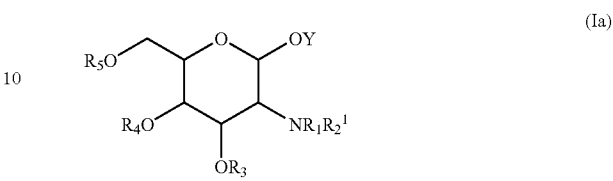

(Ia)

in which the monosaccharide ring is of the glucosamine or galactosamine configuration and the anomeric center may be either the α or β configuration;
R$_5$, R$_4$ and R$_3$ are as defined in formula I above;
R$_2^1$ is hydrogen;
R$_1$ is:
(i) a substituted acyl or optionally unsubstituted C$_{3-8}$ acyl which is substituted or optionally substituted with one or more OH, SH, CF$_3$, NO$_2$, halo, SO$_3$H, NH$_2$, CO$_2$H, azido, nitroso, alkoxy, aryloxy, SO$_2$NH$_2$, amidine or guanidinium;
(ii) a benzoyl group which may be optionally substituted with one or more OH, SH, CF$_3$, alkyl, alkenyl, alkynyl, NO$_2$, halo, SO$_3$H, NH$_2$, CO$_2$H, azido, nitroso, alkoxy, SO$_2$NH$_2$, amidine or guanidnum;
(iii) a biphenylcarbonyl group which may be optionally substituted on either one or both of the aromatic rings with one or more of OH, SH, CF$_3$, alkyl, alkenyl, alkynyl, NO$_2$, halo, SO$_3$H, NH$_2$, CO$_2$H, azido, nitroso, alkoxy, SO$_2$NH$_2$, amidine or guanidinium; or
(iv) a heteroaryl acyl, sulfonamide, urea or carbamate; or
R$_1$ and R$_2$ together form optionally substituted succinimide, optionally substituted maleimide or optionally substituted phthalimide;
Y is as defined in formula I above in which the optional substituents for Z$^1$ or Z$^{11}$ are at least one of OH, SH, CF$_3$, alkyl alkenyl alkynyl, NO$_2$, halo, SO$_3$H, NH$_2$, CO$_2$H, azido, nitroso, alkoxy, aryloxy, SO$_2$NH$_2$, amidine and/or guanidinium.

Preferably, the glycolate or lactate or derivatives thereof are optionally substituted with at least one amino acid or peptidomimetic.

Examples of suitable peptidomimetic substituents which may be used at R$_3$ are disclosed in Gante, J., Angew. Chem. Int. Ed. Engl., 1994, 33, 1699-1720 and Giannis, A., and Kolter, T., Angew. Chem. Int. Ed. Engl., 1993, 32, 1244-1267).

Non-limiting examples of carboxylic acid mitmetics and other suitable substituents for R$_3$ are:

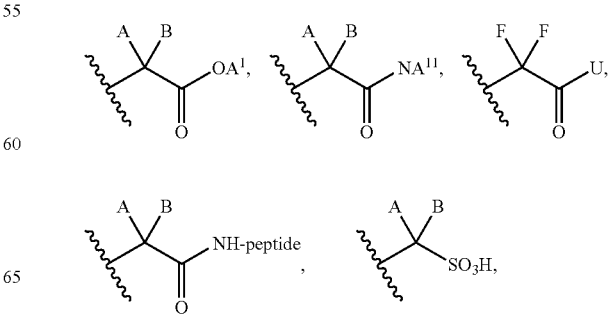

-continued

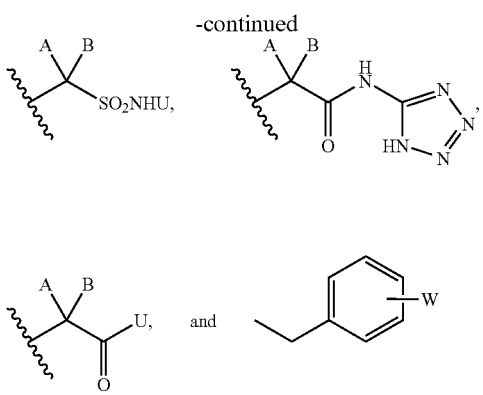

in which A and B are independently hydrogen, alkyl, trihaloalkyl or halo;

$A^1$ is hydrogen or alkyl;

$A^{11}$ is hydroxy, optionally substituted amine or oxyaryl;

U is hydrogen, aryl, heteroaryl, alkyl, alkenyl or alkynyl each of which may be optionally substituted with one or more of OH, SH, $CF_3$, alkyl, alkenyl, alkynyl, $NO_2$, halo, $SO_3H$, $NH_2$, $CO_2H$, azido, nitroso, alkoxy, $SO_2NH_2$, amidine or guanidinium; and W is hydrogen or an acidic or acid mimetic, such as, for example, OH, SH, $CF_3$, $NO_2$, halo, $SO_3H$, $CO_2H$, azido, nitroso, alkoxy, aryloxy, $SO_2NH_2$, or forms a carbocyclic or heterocyclic ring.

Another preferred compound of formula I has the formula Ib:

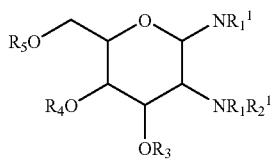

in which the monosaccharide ring substitution is of the glucosamine or galactosamine configuration and the anomeric center may be of the α or β configuration;

$R_5$, $R_4$ and $R_3$ are as defined in formula I above;

$R_2^1$ and $R_1$ are as defined in formula Ia above;

$R_1$ is $N_2$ or

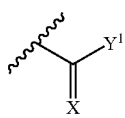

in which

X is O, NH or S; and $Y^1$ is as defined in formula I above in which $R_7$ may be optionally substituted with at least one of OH, SH, $CF_3$, alkyl, alkenyl, alkynyl, $NO_2$, halo, $SO_3H$, $NH_2$, $CO_2H$, azido, nitroso, alkoxy, $SO_2NH_2$, amidine or guanidinium.

A further preferred compound of formula I has the formula Ic:

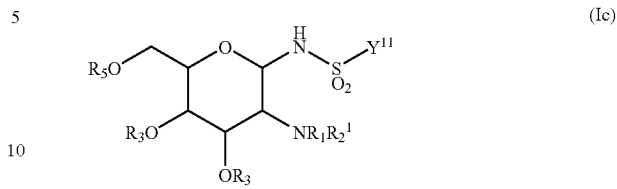

in which the monosaccharide ring substitution is of the glucosamine or galactosamine configuration and the anomeric center may be of the α or β configuration;

in which $R_5$, $R_4$ and $R_3$ are as defined in formula I above;

$R_2^1$ and $R_1$ are as defined in formula Ia above;

$Y^{11}$ is as defined in formula I above and may be optionally substituted with one or more OH, SH, $CF_3$, alkyl, alkenyl, alkynyl, $NO_2$, halo, $SO_3H$, $NH_2$, $CO_2H$, azido, nitroso, alkoxy, $SO_2NH_2$, amidine or guanidinium.

The invention also provides a method for the preparation of a compound of formula I, comprising the step of glycosylating an intermediate compound of formula IV:

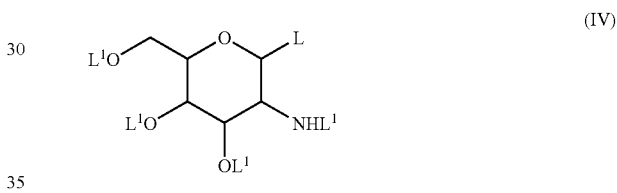

in which L is a leaving group and $L^1$ is a protecting group, with an alcohol or phenol acceptor.

The leaving group may be of any suitable known type, such as, for example, those leaving groups disclosed in J. March, "Advanced Organic Chemistry: Reactions, Mechanisms and Structure", 4th Edition, pp 352-357, John Wiley & Sons, New York, 1992 which is incorporated herein by reference. Preferably, the leaving group is acetate, thiomethyl, trichloroacetimidyl or halogen, more preferably bromine or chlorine.

Suitable protecting groups include those disclosed in Greene, T. W., "Protective Groups in Organic Synthesis", John Wiley & Sons, New York, 1981, such as optionally substituted silyl, optionally substituted alkyl optionally substituted acyl or optionally substituted heteroacyl, for example, azide or 4,4-dimethyl-2,6-dioxocyclohex-1-ylidene (Dde), tert-butyldimethylsilyl, tert-butyldiphenylsilyl, benzylidene, 4-methoxybenzylidene, benzoate, acetate, chloroacetate, 9-fluorenylmethylcarbamate, benzyloxy carbamates, isopropylidene and 4-methoxyphenyl.

Examples of suitable alcohols include methanol, ethanol, propanol, isopropanol, benzyl alcohol, 2',2-chloroethoxyethanol, 2",2',2-chloroethoxyethoxyethanol, 2-naphthylmethanol, 1-naphthylmethanol, allyl alcohol, 5-pentenol, 4-butenol, tert-butanol, sec-butanol and n-butanol.

Examples of suitable "phenol acceptors" include 4-nitrophenol, phenol, resorcinol, phloroglucinol, 4-chlorophenol, catechol and 4-allylphenol.

The invention further provides a method for the preparation of a compound of formula I, in particular formula Ib or Ic, comprising the step of acylating a compound of formula V:

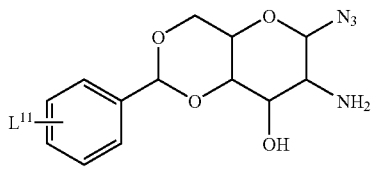

(V)

in which $L^{11}$ is hydrogen, $NO_2$, halo, azido or alkoxy.

The compounds of the present invention are useful in screening for biological activity, particularly use of compounds of the formulae Ia, Ib and Ic for screening for antibacterial or antibiotic activity. In particular, compounds of the invention are useful in screening for inhibitory activity against one or more enzymes of the muramyl cascade.

Thus, according to a further aspect of the present invention there is provided a method of screening for antibacterial or antibiotic compounds comprising the steps of:

(a) forming a combinatorial library comprising a compound of the formula I defined above; and (b) testing the combinatorial library for antibacterial or antibiotic activity.

According to a still further aspect of the present invention there is provided an antibacterial or antibiotic compound identified using the method defined above.

In a particularly preferred embodiment for this purpose, the compound of formula Ia has the structure A:

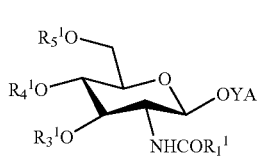

(A)

in which $R_5^1$ and $R_4^1$ are hydrogen or together form a benzylidene-type acetal;

$R_3^1$ is a lactate or lactate mimetic which may be optionally substituted with short peptides or peptidomimetics such as those found in the muramyl enzyme products;

$R_1^1$ is an acetyl group as in the naturally-occurring system; or $NHCOR_1^1$ is an other amide, a sulfonamide, a urea and the like; and YA is a structural or functional mimetic of uridine diphosphate or a simple diphosphate.

Analogous compounds to Structure A of the formulae Ib and Ic of the invention are also contemplated as preferred embodiments for this purpose.

The compounds and processes described herein are particularly suited to the solid and solution phase combinatorial synthesis of carbohydrate-based libraries, and are amenable to automation. The methods of the invention yield common intermediates which are suitably functionalized to provide diversity in the structure of the compounds so generated. In this way the technology described can produce many and varied compounds around the basic structure shown in formula I. Using this method, it is possible to introduce varied functionality in order to. modulate both the biological activity and pharmacological properties of the compounds generated.

BRIEF DESCRIPTION OF THE DRAWING

FIG. 1 is an HPLC and mass spectrum of 1-[2'-(2"-(4"'-chlorophenylthio)ethoxy)ethyl]-2-deoxy-2-benzoylamino-β-D-glucose.

FIG. 2 is an HPLC and mass spectrum of 1-[2'-(2"-(2"'-(m-trifluoromethylphenylthio) -ethoxy)ethoxy)ethyl]-2-deoxy-2-acetylamino-β-D-glucose.

FIG. 3 is an HPLC and mass spectrum of 1-[2'-(2"-(2"'-(m, p-dichlorophenylthio)ethoxy)-ethoxy)ethyl]-2-deoxy-2-(3', 3',3'-trimethyl-propionylamino)-β-D-glucose.

FIG. 4 is a $^1H$ NMR spectrum of 1-[2'-(2"-(2"'-chloroethoxy)ethoxy)ethyl]-2-deoxy-2-benzoyl-amino-4,6-O-benzylidene-3-O-methylcarbonyl-[((α-O-benzyl)-γ-glutamyl)-($N^6$-(2'-chlorobenzyl-carbamoyl)lysinyl)-(O-benzylalanyl)]-β-D-glucopyranoside.

FIG. 5 is a mass spectrum of 1-[2'-(2"-(2"'-chloroethoxy)ethoxy)ethyl]-2-deoxy-2-benzoyl-amino-4,6-O-benzylidene-3-O-methylcarbonyl-[((α-O-benzyl)-γ-glutamyl)-($N^6$(2'-chlorobenzyl-carbamoyl)lysinyl)-(O-benzylalanyl)]-β-D-glucopyranoside.

DETAILED DESCRIPTION OF THE INVENTION

The invention will now be described in detail by way of reference only to the following non-limiting examples and to the drawings.

Abbreviations used herein are as follows:
MeCN acetonitrile,
Ether diethyl ether;
DCM methylene chloride; dichloromethane,
MeOH methanol,
EtOAc ethyl acetate,
DMF N,N-dimethylformamide,
HBTU O-benzotriazol-1-yl-N,N,N',N'-tetramethyuronium hexafluorophosphate,
TBAF tetrabutylammonium fluoride,
Dde 4,4-dimethyl-2,6-dioxocyclohex-1-ylidene,
BOP benzotriazol-1-yloxy-tris(dimethylamino)phosphonium hexafluorophosphate,
PyBOP benzotriazol-1-yloxy-tris(pyrrolidyl)phosphonium hexafluorophosphate,
HATU O-(7-azabenzotriazol-1-yl)-N,N,N',N'-tetramethyuronium hexafluorophosphate,
Fmoc 9-fluorenylmethylcarbamate, and
Boc t-butylcarbamate.

The term "derivatives" is used herein in its broadest sense to include protected forms and synthetic precursors of compounds of the present invention, for example, azide is a protected form/precursor of amine, nitrile is a protected form/ precursor of amine, carboxylic acid and amide.

The term "tautomer" is used herein in its broadest sense to include compounds of formula I which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of formula I may have one or more chiral centers, it is capable of existing in enantiomeric forms. The anomeric center of the monosaccharide ring may also be of either the α or β configuration.

The term "halo" denotes fluorine, chlorine, bromine or iodine, preferably fluorine, chlorine or bromine.

The term "alkyl" used either alone or in compound words such as "optionally substituted alkyl", "optionally substituted cycloalkyl", "arylalkyl" or "heteroarylalkyl", denotes straight chain, branched or cyclic alkyl, preferably $C_{1-6}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- or 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2 pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkylene" used either alone or in compound words such as "optionally substituted alkylene" denotes the same groups as "alkyl" defined above except that an additional hydrogen has been removed to form a divalent radical. It will be understood that the optional substituent may be attached to or form part of the alkylene chain.

The term "alkenyl" used either alone or in compound words such as "optionally substituted alkenyl" denotes groups formed from straight chain, branched or cyclic alkenes including ethylenically mono-, di- or poly-unsaturated alkyl or cycloalkyl groups as defined above, preferably $C_{2-6}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" used either alone or in compound words, such as "optionally substituted alkynyl" denotes groups formed from straight chain, branched, or mono- or poly- or cyclic alkynes, preferably $C_{2-6}$ alkynyl. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "alkoxy" used either alone or in compound words such as "optionally substituted alkoxy" denotes straight chain or branched alkoxy, preferably $C_{1-7}$ alkoxy. Examples of alkoxy include methoxy, ethoxy, n-propyloxy, isopropyloxy and the different butoxy isomers.

The term "aryloxy" used either alone or in compound words such as "optionally substituted aryloxy" denotes aromatic, heteroaromatic, arylalkoxy or heteroaryl alkoxy, preferably $C_{6-13}$ aryloxy. Examples of aryloxy include phenoxy, benzyloxy, 1-naphthyloxy, and 2-naphthyloxy.

The term "acyl" used either alone or in compound words such as "optionally substituted acyl" or "heteroarylacyl" denotes carbamoyl, aliphatic acyl group and acyl group containing an aromatic ring, which is referred to as aromatic acyl or a heterocyclic ring which is referred to as heterocyclic acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutyl, phenylpentanoyl and phenylhexanoyl) and naphthylalkanoyl (e.g. naphthylacetyl, naphthlpropanoyl and naphthylbutanoyl); aralkenoyl such as phenylalkenoyl (e.g. phenylpropenoyl, phenylbutenoyl, phenylmethacrylyl phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and naphthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and naphthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienyglyoxyloyl.

The term "aryl" used either alone or in compound words such as "optionally substituted aryl", "arylalkyl" or "heteroaryl" denotes single, polynuclear, conjugated and fused residues of aromatic hydrocarbons or aromatic heterocyclic ring systems. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, pyrrolyl, furanyl, imadazolyl, pyrrolydinyl, pyridinyl, piperidinyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferably, the aromatic heterocyclic ring system contains 1 to 4 heteroatoms independently selected from N, O and S and containing up to 9 carbon atoms in the ring.

The term "heterocycle" used either alone or in compound words as "optionally substituted heterocycle" denotes monocyclic or polycyclic heterocyclyl groups containing at least one heteroatom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pytidyl, pyriridinyl, pyrazinyl, pyridazinyl, triazolyl or tetrazolyl;

saturated to 3 to 6-membered heteromonocyclic groups containing 1 to 4 nitrogen atoms, such as, pyrrolidinyl, irnidazolidinyl, piperidino or piperazinyl;

unsaturated condensed heterocyclic groups containing 1 to 5 nitrogen atoms, such as, indolyl, isoindolyl, indolizinyl, benzitidazoyl, quinolyl, isoquinolyl, indazol l, benzotriazolyl or tetrazolopyridazinyl; unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as thiazolidinyl; and unsaturated condensed heterocyclic group containing 1 to 2 sulphur atoms and 1 to 3 nitrogen atoms, such as, benzothiazolyl or benzothiadiazolyl.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, carboxy, benzyloxy, haloalkoxy, haloalkenyloxy, haloaryloxy, nitro, nitroalkyl, nitroalkenyl, nitroalkynyl, nitroaryl, nitroheterocyclyl, nitroso, azido, amidine, guanidinium, amino, alkylarnino, alkenylanino, alkynylanino, arylamino, benzylarmino, acylamino, acyl, alkenylacyl, alkynylacyl, arylacyl, acylamnino, acyloxy, aldehydo, alkylsulphonyl, arylsulphonyl, sulphonylarnino, alkylsulphonylarmino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, sulfonic acid, alkylthio, arylthio, acylthio and peptidomimetics.

Preferred optional substituents include OH, SH, $CF_3$, alkyl, alkenyl, alkynyl, $NO_2$, halo, $SO_3H$, $NH_2$, $CO_2H$, azido, nitroso, alkoxy, aryloxy, $SO_2NH_2$, amidine, guandinium and peptidomimetics.

For the purposes of this specification it will be clearly understood that the word "comprising" means "including but not limited to", and that the word "comprises" has a corresponding meaning.

Exemplary compounds of the invention were prepared as set out in the following synthetic schemes 1 to 3 and detailed in the general procedures.

All final compounds were purified by liquid chromatography-mass spectrometry (LC-MS), using a micromass LCZ electrospray mass spectrometer as detector. Proton NMR results are included for representative compounds.

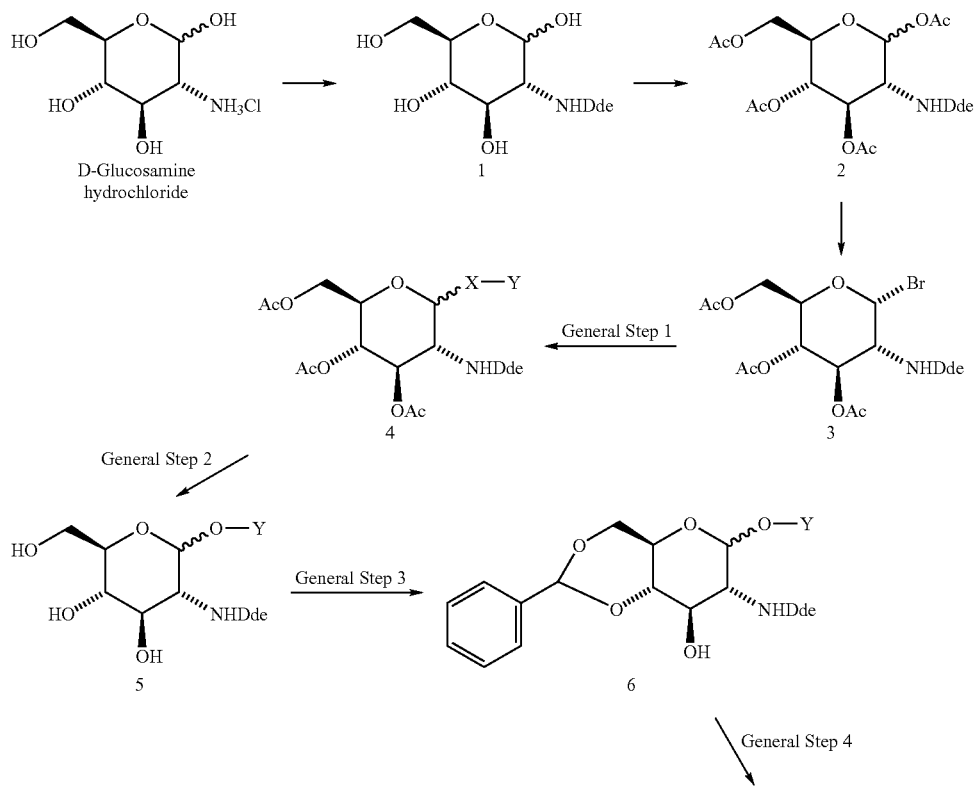

Scheme 1

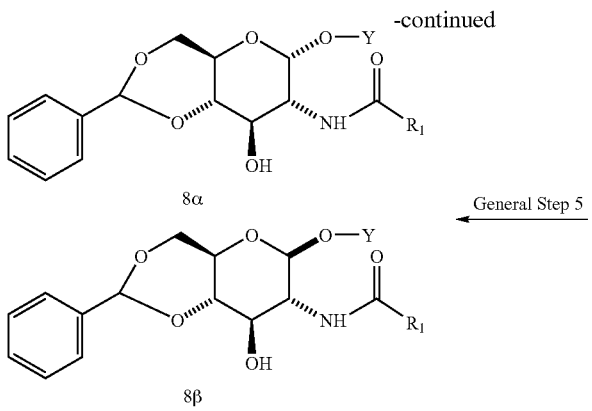

8α

8β

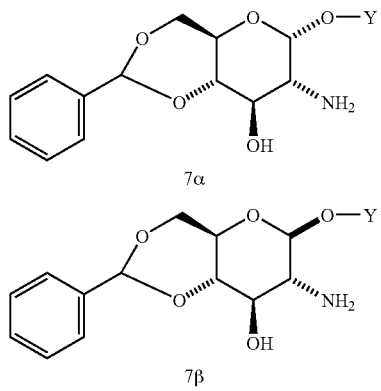

7α

7β

Y=benzyl, naphthylmethyl, 2'-chloroethoxyethyl 2"-chloroethoxyethoxyethyl.

R₁=methyl, phenyl, tert-butyl, tert-butylmnethylene, biphenyl.

2-Deoxy-2-[1-(4,4-dimethyl-2,6-dioxocyclohex-1-ylidene)-ethylamino]-α-D-glucopyranose (1)

Glucosatmine hydrochloride (50 g, 231 mmol) was suspended in anhydrous methanol (500 mL), then 2-acetyldirnedone sodium salt (47.3 g, 231 mmol) was added. The reaction mixture was stirred at room temperature for 10 minutes, then 2-acetyl-dirnedone (21.1 g, 115.9 mmol) was added. The reaction mixture was stirred under reflux for 2.5 hours and monitored by tlc. At the completion of the reaction (TLC: MeCN-$H_2O$, 10:2), the reaction mixture was cooled to room temperature and filtered. The filtrate was evaporated and the resulting solid residue was washed on a funnel with ether (3×500 mL) and dried to give crude product (75 g, 94%). No further purification was required for the next reaction.

1,2,4,6-Tetra-O-acetyl-2-deoxy-2-[1-(4,4-ditnethyl-2,6-dioxocyclohex-1-ylidene)-ethylamino]-α-D-glucopyranose (2)

Crude 2-deoxy-2-[1-(4,4-dimethyl-2,6-dioxocyclohex-1-ylidene)-ethylanimo]-α,β-D-gluco-pyranose (75 g, 218.6 mmol) was dissolved in pyridine (320 mL) and acetic anhydride (165 mL) was added dropwise keeping the temperature below 30° C. The reaction mixture was stirred overnight then solvents evaporated. Toluene (2×100 mL) was evaporated off the residue. The residue was taken up in $CH_2Cl_2$ (550 mL), washed with 5% HCl solution (280 mL), water (3×1 L), saturated $NaHCO_3$ (1 L), then dried over $MgSO_4$ and the solvents evaporated. The product was crystallised from MeOH (250 mL), filtered, and washed with cold MeOH (−40° C.) on the funnel. The solid was dried to give 1,2,4,6-tetra-O-acetyl-2-deoxy-2-[1-(4,4-dimethyl-2,6-dioxocyclohex-1-ylidene)-ethylamino]-α-D-glucopyranose (95 g, 85%).

3,4,6-Tri-O-acetyl-2-deoxy-2-[1-(4,4-dimethyl-2,6-dioxocyclohex-1-ylidene)-ethylamino]-α-D-glucopyranosyl bromide (3)

1,2,4,6-Tetra-O-acetyl-2-deoxy-2-[1-(4,4-dimethyl-2,6-dioxocyclohex-1-ylidene)-ethylamino]-α-D-glucopyranose (150 g, 293.5 mmol) was dissolved in dry $CH_2Cl_2$ (300 mL) and hydrogen bromide in acetic acid (400 mL, 30%) was added. The reaction mixture was stirred at room temperature for 2 hours, then diluted with cold $CH_2Cl_2$ (−15° C., 2 L) and washed with cold water (0° C., 3×2 L), and saturated $NaHCO_3$ (2 L). The organic phase was dried over $MgSO_4$ and evaporated in vacuo at 30° C. The resulting white solid residue was suspended in ether (1 L) and filtered. The solid was dried under vacuum giving 3,4,6-tri-O-acetyl-2-deoxy-2-[1-(4,4-dimethyl-2,6-dioxocyclohexa-1-ylidene)-ethylamino]-α-D-glucopyranosyl bromide (150 g, 95%). $R_f$ 0.62 (EtOAc/Hexane 2:1); MS (electrospray) $C_{22}H_{30}BrNO_9$ (532.1/534.0) m/z (%) 533.38/535.38 [M+H]$^+$ (100).

General Step 1: Reaction of 3 with Acceptor Alcohols

A mixture of 3,4,6-tri-O-acetyl-2-deoxy-2-[1-(4,4-ditnethyl-2,6-dioxocyclohex-1-ylidene)-ethylamino]-β-D-glucopyranosyl bromide (3) (1 equivalent), the acceptor alcohol (1.5 equivalents) and activated molecular sieves (equal mass as bromide 3) were stirred in 1,2-dichloroethane (10 mL per gram of 3) under a nitrogen atmosphere at −78° C. in a flask that had been covered to preclude ambient light. Silver triflate (1.45 equivalents) was added and the mixture allowed to warm to room temperature. This reaction was then stirred at room temperature for 1 hour, diluted with $CH_2Cl_2$ (20 mL per gram of 3), and filtered through a plug of Celite. The eluent was then washed with saturated $NaHCO_3$ (3×10 mL per gram of 3), dried over $MgSo_4$, and the solvent removed in vacuo to yield an anomeric mixture of the glycosylated compounds.

Acceptor A=2-(2-chloroethoxy)ethoxy)ethanol, amount of (3) used 21 g, yield 4A 20.57 g (84%). MS (electrospray) $C_{28}H_{42}ClNO_{12}$ (619.3/621.2) m/z (%) 620.32/622.4 [M+H]$^+$ (100).

Acceptor B=2-(2-chloroethoxy)ethanol, amount of (3) used=35 g, yield 4B 37 g 97%.

Acceptor C=2-naphthylmethanol, amount of (3) used 34.5 g, yield 4C 25.75 g (66%).

MS (electrospray) $C_{33}H_{39}NO_{10}$ (609) m/z (%) 610[M+H]$^+$ (100).

Acceptor D=benzyl alcohol, amount of (3) used 2.24 g, yield 4D 2.35 g.

General Step 2: Deacylation of Glycosylation Products 4

Products of general step 1 (1 eq) were dissolved in methanol (4 rnL per gram of substrate) and sodium metal (10 mg per gram of substrate dissolved in methanol) was added. The reaction vessel was fitted with a calcium chloride guard tube and the mixture strrred at room temperature for 30 minutes with monitoring by tlc (EtOAc/hexane 2:1). When the reaction was complete Amberlite IR-120 (H) cation exchange resin was added to the mixture until slightly acidic (pH 5-6). The resin was filtered off and the solvent removed in vacuo. The residue was further purified by passing through a short column of silica gel and eluting with MeCN/water (10:1). Solvents were removed to yield the desired triols 5A, 5B, and 5C.

5A): Amount of substrate 4A 41.30 g, yield 30.98 g (940/). MS (electrospray) $C_{22}H_{36}ClNO_9$ (493.2,495.1) m/z (%) 494, 496 [M+H]$^+$ (30); (516.1, 518.2) m/z (%) 516, 518 [M+Na]$^+$ (100).

5B): Amount of substrate 4B 37 g, yield 28.5 g (97%).

5C): Amount of substrate 4C 25.70 g, yield 18.24 g (890/). MS (electrospray) $C_{27}H_{33}NO_7$ (483) m/z (%) 484 [M+H]$^+$ (100); (507) m/z (%) 507 [M+Na]$^+$ (35).

General Step 3: Benzylidene Acetal Formation

Product from general step 2 (5A, 5B, 5C) 1 equivalent was dissolved in dry acetonitrile (7.5 mL per gram of substrate), benzaldehyde dimethyl acetal (2 equivalents) and para-toluenesufonic acid monohydrate (2 mg per gram of substrate) were added. The flask was fitted with a calcium chloride guard tube and the mixture stirred at 60° C. for 14 hours, after which triethylamine (1 mL) was added and the solvent removed in vacuao. The residue was taken into $CH_2Cl_2$ (20 mL per gram of substrate) and washed with brine (3 times 5 mL per gram of substrate), dried (MgSO$_4$) and the residue triturated with ether/petrol. The solvent was then removed in vactuo to yield the desired acetals as a white solid. The product was used without further purification in the next step.

General Step 4: Removal of Dde

The product of general step 3 (6A to 6C) was dissolved in a mixture of methanol and aqueous ammonia (28%) 1:1 (20 mnL per gram of substrate) and warmed to 60° C. for 14 hours. The solvents were removed in vacuao and the residue purified by column chromatography (gradient acetonitrile to acetonitrile methanol 1:1) to yield both the α and β anomers as pure components.

Amount of substrate crude 5A 76.5 g, yield 7Aα 20.6 g (38%), yields are over 3 steps. MS (electrospray) $C_{19}H_{28}ClNO$ (417, 419) m/z (%) 418, 420 [M+H]$^+$ (100), 250 (70).

Yield 7Aβ 12.6 g (23%), MS (electrospray) $C_{19}H_{28}ClNO$ (417, 419) m/z (%) 418, 420 [M+H]$^+$ (100).

Amount of substrate pure 5B 34.1 g,

Yield 7Bα 8.16 g (34%),

Yield 7Bβ 14.86 g (62%).

Amount of substrate crude 5C 20.30 g,

Yield 7Cα 1.2 g, yields are over 3 steps. $^1$H NMR (500 MHz, CD$_3$OD) δ 7.30-8.10 (14H mn aromatics+NH$_2$), 5.55 (1H s Ph-[C$\underline{H}$)], 5.20 (1H d J=12 naphthyl CH$_a$), 5.00 (1H d J=12 naphthyl CH$_b$), 4.95 (1H d J=4 H-1), 4.25 (1H dd J=5,10 H-4), 3.90-4.00 (1H m H-5), 3.75-3.80 (2H m H-6), 3.50 (1H t J=9.5 H-3), 2.80-2.85 (1H m H-2).

Yield 7Cβ 6.58 g. MS (electrospray)$C_{24}H_{25}NO_5$ (407) m/z (%) 408 [M+H]$^+$ (100). $^1$H NMR (500 MHz, CD$_3$OD) δ 7.35-8.15 (14H m aromatics+NH$_2$), 5.55 (1H s Ph-C$\underline{H}$), 5.40 (1H d J=12 naphthyl CH$_a$), 5.05 (1H d J=12 naphthyl CH$_b$), 4.45 (1H d J=8 H-1), 4.40 (1H dd J=5,10 H-4), 3.85 (1H t J=10 H-3), 3.55-3.65 (2H m H-6), 3.45-3.5 (1H m H-5), 2.80-2.90 (1H m H-2).

General Step 5: Selective Acylation of Free Amnine

The products of general step 4 (7Aα, 7Aβ, 7Bα, 7Bβ, 7Cα, and 7Cβ) were dissolved in dry methanol (10 mL per gram of substrate, dry dichloromethane may be substituted for methanol) and the solution stirred at room temperature. Where available the symmetrical anhydride of the acylating agent was added (1.05 equivelants). In the case of the biphenylcarbonyl, tert-butylacetyl and tert-butylcarbonyl acyl groups the acid chloride was used. In many cases the product began to precipitate after 5 minutes and the product was collected after 30 minutes by filtration. The solid was washed with a small amount of cold methanol. In cases where the product did not precipitate, the product was partitioned between dichloromethane and sodium hydrogen carbonate solution, and the organic layer was dried and evaporated to yield the desired product. The yields are summarized in Table 1.

TABLE 1

NMR data and yields for general step 5 of Scheme 1

|  | 7Aα yield | 7Aβ yield | 7Aα H-1 shift | 7Aβ H-1 shift |
|---|---|---|---|---|
| 1) Acetyl | 74% | 89% | Not recorded | 4.53 d J = 8.0 |
| 2) Benzoyl | 69% | 82% | 4.95 d J = 4.0 | 4.71 d J = 8.0 |
| 3) Biphenylcarbonyl | 80% | 73% | Not recorded | 4.66 d J = 7.0 |
| 4) tert-Butylcarbonyl | 74% | 84% | Not recorded | 4.75 d J = 9.0 |
| 5) tert-Butylacetyl | 68% | 80% | Not recorded | 4.85 d J = 9.0 |

|  | 7Bα yield | 7Bβ yield | 7Bα H-1 shift | 7Bβ H-1 shift |
|---|---|---|---|---|
| 1) Acetyl | 44% | 86% | 4.72 d J = 4.0 | 4.77 d J = 8.4 |
| 2) Benzoyl | 66% | 75% | Not recorded | 3.86 d J = 7.7 |
| 3) Biphenylcarbonyl | 87% | 86% | Not recorded | 3.88 d J = 7.8 |
| 4) tert-Butylcarbonyl | 85% | 69% | Not recorded | 4.87 d J = 8.3 |
| 5) tert-Butylacetyl | 76% | 77% | 4.56 d J = 3.0 | 4.79 d J = 8.4 |
| 6) 2-Nitrophenacetyl | Not done | 83% | Not done | Not recorded |

|  | 7Cα yield | 7Cβ yield | 7Cα H-1 shift | 7Cβ H-1 shift |
|---|---|---|---|---|
| 1) Acetyl | 61% | 87% | 5.10 d J = 3.0 | 4.85 d J = 8.0 |
| 2) Benzoyl | 75% | 89% | Not recorded | 4.90 d J = 8.0 |
| 3) Biphenylcarbonyl | 87% | 82% | 5.25 d J = 4.0 | 4.90 d J = 8.0 |
| 4) tert-Butylcarbonyl | 58% | 83% | Not recorded | 4.90 d J = 8.0 |
| 5) tert-Butylacetyl | 68% | 80% | Not recorded | 4.85 d J = 8.2 |

Expected masses were observed for each compound and 1H NMR spectra were recorded for selected compounds.

General Step 6: Alkylation of C-3 Hydroxyl

The products of general step 5 (8Aα, 8Aβ, 8Bα, 8Bβ, 8Cα, and 8Cβ) with their appropriate acyl groups on nitrogen as indicated in the tables above (1 equivalent) were dried under high vacuum and added to a stirred suspension of 95% sodium hydride (2 equivalents) in dry N,N-dimethylformarmide at 0° C. under nitrogen. The mixture was stirred for 30 minutes, then the alkylating agent (methyl bromoacetate: 2 equivalents) was added and the reaction mixture allowed to warm to room temperature. The reaction was monitored by LC-MS for disappearance of starting alcohol. Typically reactions proceeded over 3 hours; however in some instances, the mixture was stirred overnight. The reaction mixture was worked up by cooling the mixture to 0° C. and quenching unreacted sodium hydride with methanol. Solvents were removed in vacuo, and the residue taken up in dichloromethane and extracted with 10% citric acid, saturated sodium chloride then dried over anhydrous magnesium sulphate and concentrated.

In cognate preparations tert-butyl bromoacetate and benzyl bromoacetate have been used as the alkylating agent.

$^1$H NMR spectra were recorded for 10 example products of this reaction. In each case a characteristic methyl singlet at δ 3.45 was observed corresponding to the methyl ester group. The location and coupling constant of the anomeric proton remained essentially unchanged.

Exemplary yield and mass spectral data are shown in Table 2.

TABLE 2

MS data and yields for general step 6 of Scheme 2

| Compound | Yield | M + H (%) |
|---|---|---|
| 9Cβ acetate | 76% | 522 (100) |
| 9Cβ benzoate | 66% | 584 (100) |
| 9Cβ biphenylformate | 82% | 660 (100) |
| 9Cβ tert-butylformate | 78% | 564 (100) |
| 9Cβ tert-butylacetate | 87% | 578 (100) |
| 9Aβ acetate | 90% | 532 (50) |
| 9Aβ benzoate | 78% | 594 (100) |
| 9Aβ biphenylformate | 59% | 670 (100) |
| 9Aβ tert-butylformate | 84% | |
| 9Aβ tert-butylacetate | 77% | |
| 9Bβ acetate | 88% | |
| 9Bβ benzoate | 53% | |
| 9Bβ biphenylformate | 81% | |
| 9Bβ tert-butylformate | Not recorded | |
| 9Bβ tert-butylacetate | Not recorded | |

TABLE 2-continued

MS data and yields for general step 6 of Scheme 2

| Compound | Yield | M + H (%) |
|---|---|---|
| 9Cα acetate | 77% | 522 (100) |
| 9Cα benzoate | 62% | 584 (100) |
| 9Cα biphenylformate | 63% | 660 (100) |
| 9Cα tert-butylformate | 98% | 564 (100) |
| 9Cα tert-butylacetate | 44% | 578 (100) |
| 9Aα acetate | 74% | 532 (50) |
| 9Aα benzoate | 87% | 594 (100) |
| 9Aα biphenylformate | 79% | 670 (100) |
| 9Aα tert-butylformate | 68% | |
| 9Aα tert-butylacetate | 74% | |
| 9Bα acetate | Not recorded | |
| 9Bα benzoate | 93% | 550 (80) |
| 9Bα biphenylformate | Not recorded | 626 (100) |
| 9Bα tert-butylformate | 55% | 530 (70) |
| 9Bα tert-butylacetate | 89% | 544 (95) |

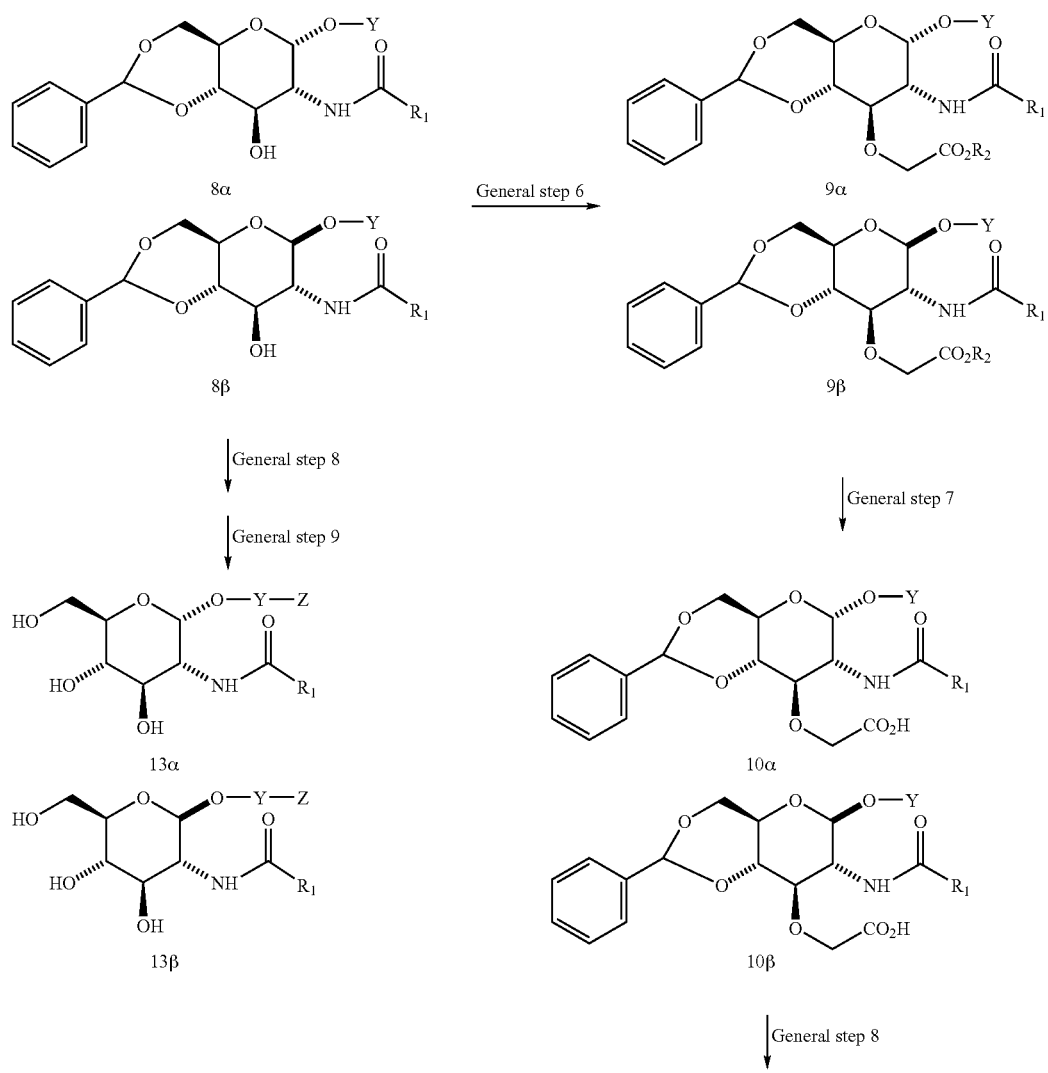

Scheme 2

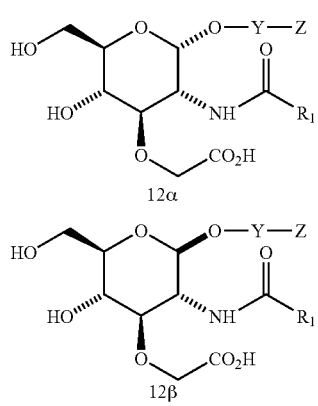

-continued

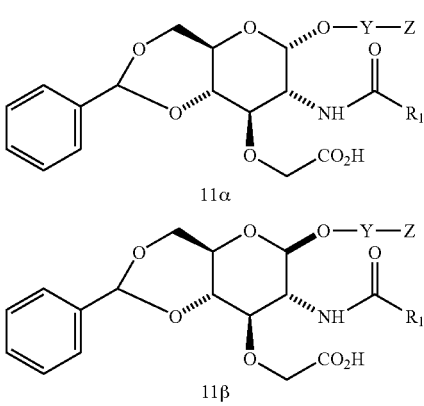

R₂=methyl, benzyl, tert-butyl
R₁ and Y are as defined in scheme 1 above
Z is —S-(4-methoxy)phenyl; —S-(4-methyl)phenyl; —S-(4-chloro)phenyl; —S-(3,4-dichloro)phenyl; —S-(3-trifluoromethyl)phenyl General Step 7: Ester Hydrolysis The products of general step 6 (9Aα, 9Aβ, 9Bα, 9Bβ, 9Cα, and 9Cβ) with their appropriate acyl groups on nitrogen as indicated in the tables above were hydrolysed by treatment of a solution of the ester in tetrahydrofuran/methanol (3:2, approx 10 mL per gram of substrate) with aqueous sodium hydroxide (1M, 2 equivalents). Removal of the solvents in vacuo yielded the sodium salt of the corresponding acid and sodium hydroxide as crude product (10Aα, 10Aβ, 10Bα, 10Bβ, 10Cα, and 10Cβ) with their appropriate acyl groups on nitrogen.

General Step 8: Thiol Displacement of Halide

The substrate was dissolved in N,N-dimethylformamide and treated with the appropriate thiol (1.3 equivalents) which was pre-evaporated from 1.3 equivalents of sodium methoxide. 1.3 equivalents of sodium iodide was added to the solution and the mixture stirred overnight at room temperature under nitrogen. After this time, the solvents were removed in vacuo and the crude preparation passed through a plug of silica gel with ethyl acetate eluent, to yield essentially pure product.

Exemplary products are shown in Table 3. M+H ion and relative intensity are shown. Yields, where shown, are purified yields.

TABLE 3

| | MS data/yields for general step 8 of Scheme 2 | | | | |
|---|---|---|---|---|---|
| Substrate | 4-methyl-thiophenol | 4-methoxy-thiophenol | 4-chloro-thiophenol | 3,4-dichloro-thiophenol | 3-trifluoromethyl-thiophenol |
| 10Aβ benzoate | 668 (80) | | | | |
| 10Aβ acetate | 606 (80) | | | | |
| 10Aβ biphenyl formate | 744 (100) | | | | |
| 10Bβ acetate | 562 (70) | | | | |
| 10Bβ biphenyl formate | 700 (50) | | | | |
| 10Bβ benzoate | 623 (65) | | | | |
| 8Aβ acetate | 549 (10%) | 565 (10%) | 569 (15%) | 603 (3%) | 603 (3%) |
| | 53% yield | 91% yield | 89% yield | 64% yield | 80% yield |
| 8Aβ benzoate | 611 (6%) | 627 (5%) | 631 (8%) | 665 (4%) | 665 (3%) |
| | 34% yield | 29% yield | 39% yield | 42% yield | 40% yield |
| 8Aβ biphenyl formate | quant. yield (crude) | quant. yield (crude) | quant. yield (crude) | quant. yield (crude) | quant. yield (crude) |
| 8Aβ tert-butyl formate | 591 (10%) | 607 (10%) | 611 (5%) | 646 (12%) | 645 (15%) |
| | 67% yield | 89% yield | 78% yield | 89% yield | 74% yield |
| 8Aβ tert-butyl acetate | 605 (9%) | 621 (16%) | 625 (3%) | 659 (12%) | 659 (13%) |
| | 30% yield | 43% yield | 77% yield | 39% yield | 30% yield |
| 8Aα acetate | 549 (15%) | 565 (10%) | 569 (17%) | 603 (12%) | 603 (7%) |
| | 71% yield | 96% yield | 93% yield | 56% yield | 86% yield |
| 8Aα benzoate | 611 (7%) | 627 (1%) | 631 (20%) | 665 (1%) | 665 (1%) |
| | 33% yield | 28% yield | 23% yield | 35% yield | 26% yield |

TABLE 3-continued

MS data/yields for general step 8 of Scheme 2

| Substrate | 4-methyl-thiophenol | 4-methoxy-thiophenol | 4-chloro-thiophenol | 3,4-dichloro-thiophenol | 3-trifluoromethyl-thiophenol |
|---|---|---|---|---|---|
| 8Aα biphenyl formate | Not prepared | Not prepared | Not prepared | Not prepared | Not prepared |
| 8Aα tert-butyl formate | 591 (11%) 45% yield | 607 (17%) 46% yield | 611 (15%) 46% yield | 646 (13%) 47% yield | 645 (27%) 47% yield |
| 8Aα tert-butyl acetate | 605 (17%) 20% yield | 621 (26%) 43% yield | 625 (11%) 35% yield | 659 (10%) 41% yield | 659 (21%) 41% yield |
| 8Bβ acetate | 504 (26%) 74% yield | 520 (40%) 70% yield | 524 (30%) 67% yield | 558 (25%) 81% yield | 558 (37%) 81% yield |
| 8Bβ benzoate | 566 (19%) 42% yield | 582 (7%) 83% yield | 586 (10%) 73% yield | 621 (3%) 66% yield | 620 (10%) 75% yield |
| 8Bβ biphenyl formate | 72% yield | 75% yield | 37% yield | 83% yield | 80% yield |
| 8Bβ tert-butyl formate | 546 (20%) 79% yield | 562 (10%) 97% yield | 566 (10%) 97% yield | 600 (4%) 71% yield | 600 (11%) 73% yield |
| 8Bβ tert-butyl acetate | 560 (14%) 72% yield | 576 (9%) 68% yield | 580 (7%) 69% yield | 614 (3%) 99% yield | 614 (9%) 75% yield |
| 8Bα acetate | 70% yield | 50% yield | 66% yield | 81% yield | 59% yield |

General Step 9: Benzylidene Cleavage

The benzylidene compounds were taken up in methanol and acetonitrile (100 mg of compound in 1 mL of acetontirile and 2 mL methanol) and treated with amberlite IRA (H$^+$ form) at 45° C. for 12 hours. After this time the resin was removed by filtration and the solvents evaporated in vacuo. The products were purified by reverse phase HPLC with mass based detection.

Exemplary $^1$H NMR data:

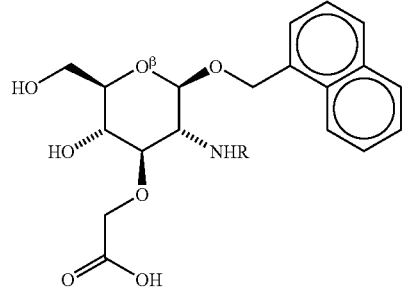

R=acetate: δ 7.35-8.05, m, 7H (aromatics); 5.35, d, J=12.0, 1H (benzylic); 4.95, d, J=12.0, 1H (benzylic); 4.55, d, J=8, 1H (H-1); 3.15-4.05, m, 8H; 1.80, s, 3H (acetate CH$_3$);
R=benzoate: δ 7.10-8.35, m, 12H (aromatics); 5.20, d, J=12.0, 1H (benzylic); 5.00, d, J=12.0, 1H (benzylic); 4.65, d, J=8, 1H (H-1); 3.20-4.20, m, 8H;
R=biphenylcarbonyl: δ 7.10-8.30, m, 16H (aromatics); 5.25, d, J=12.0, 1H (benzylic); 5.00, d, J=12.0, 1H (benzylic); 4.70, d, J=8, 1H (H-1); 3.20-3.90, m, 8H;
R=tert-butylcarbonyl: δ 7.30-8.10, m, 7H (aromatics); 5.25, d, J=12.0, 1H (benzylic); 5.00, d, J=12.0, 1H (benzylic); 4.65, d, J=8, 1H (H-1); 3.20-4.15, m, 8H; 0.95, s, 9H (tert-butyl 3×CH$_3$).

Exemplary HPLC and mass spectral data products are shown in the attached Figures.

FIG. 1 shows the LC-MS data for 1-[2'-(2''-(4'''-chlorophenylthio)ethoxy)ethyl]-2-deoxy-2-benzoylamino-β-D-glucose:

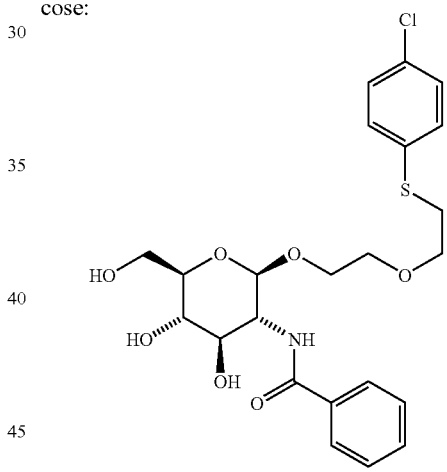

FIG. 2 shows the LC-MS data for 1-[2'-(2''-(2'''-(m-trifluoromethylphenylthio)-ethoxy)ethoxy)ethyl]-2-deoxy-2-acetylamino-β-D-glucose:

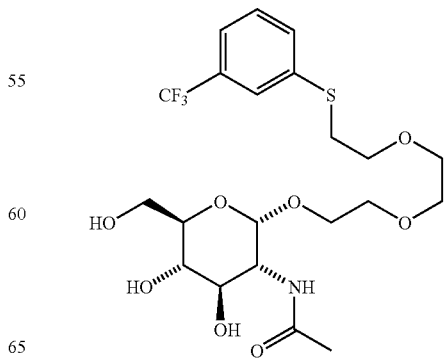

FIG. 3 shows the LC-MS data for 1-[2'-(2''-(2'''-(m,p-dichlorophenylthio)ethoxy)ethoxy)ethyl]-2-deoxy-2-(3',3',3'-trimethyl-propionylarnino)-β-D-glucose:

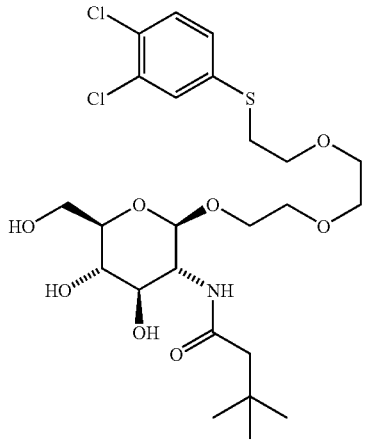

General Step 10: Coupling of Groups to the C-3 Acid Moiety

Acid substrates 10 are dissolved in N,N-dimethylformamide and activated with HBTU in the presence of triethylamine. Peptides with one free amine, amino acids with one free amine or other nucleophilic amines are added in excess and the mixture stirred for 2 hours. After this time the solvents are removed in vacuao and the crude material chromatographed on silica gel to yield the desired product.

In a specific example, substrate 10Aβ benzoate was reacted with the tripeptide α-O-benzyl-γ-glutamyl-ω-(2-chlorobenzylcarbamoyl)-lysinyl-O-benzyl-alanine to yield the desired protected product 1-[2'-(2''-(2'''-chloroethoxy)ethoxy)ethyl]-2-deoxy-2-benzoylarrino-4,6-O-benzylidene-3-O-methyl-carbonyl-[((α-O-benzyl)-γ-glutamyl)-(N$^6$(2'-chlorobenzyl-carbamoyl)lysinyl)-(O-benzylalanyl)]-β-D-glucopyranoside. HPLC and mass spectral data are shown in FIGS. 4 and 5.

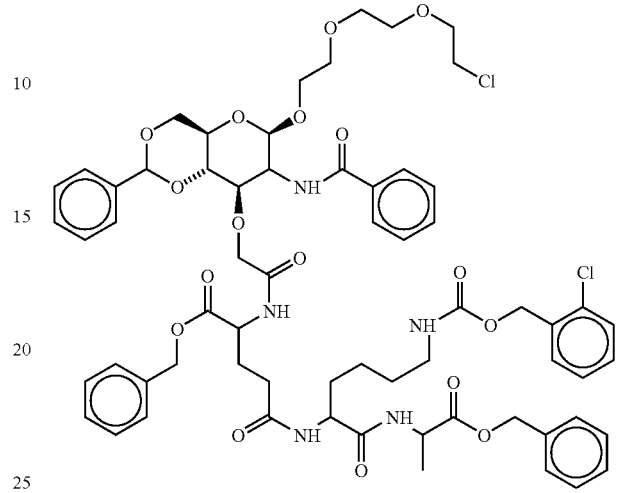

In this instance the benzyl and o-chloro-benzyloxycarbonyl protecting groups were removed by hydrogenolysis in methanol with 10% palladium on charcoal as catalyst (1% w/w Pd; 40 psi, 2 hours). The benzylidene was subsequently removed as described in general step 9. In a cognate experiment in which alanine tert-butyl ester was used, the tert-butyl protecting group and the benzylidene were removed by general step 9. It is expected that BOC amine protecting groups will be similarly amenable to this latter deprotection strategy.

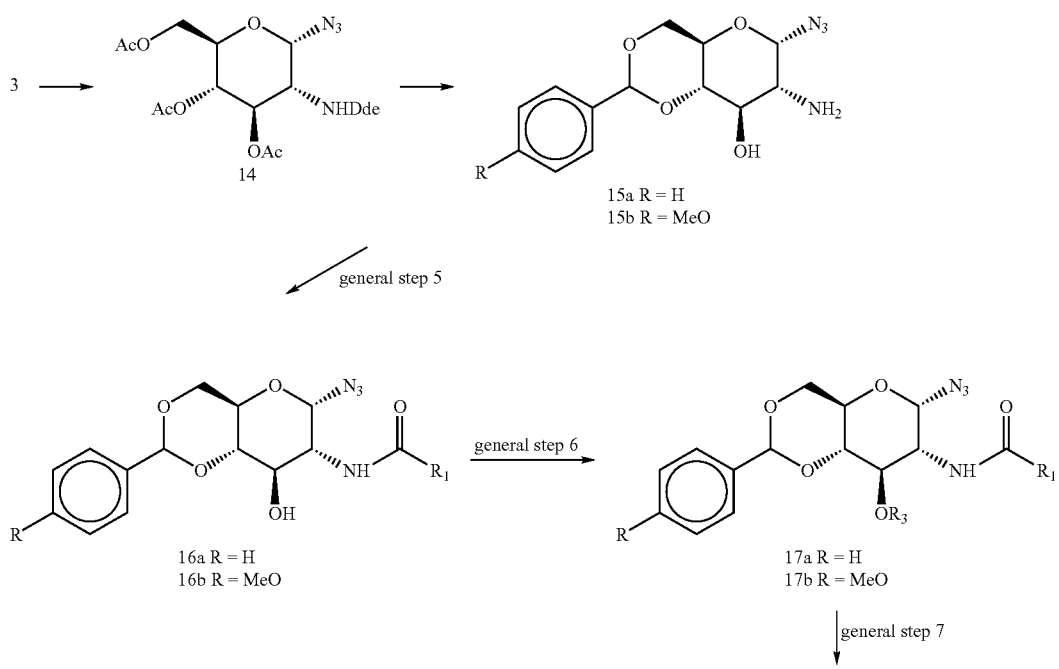

Scheme 3

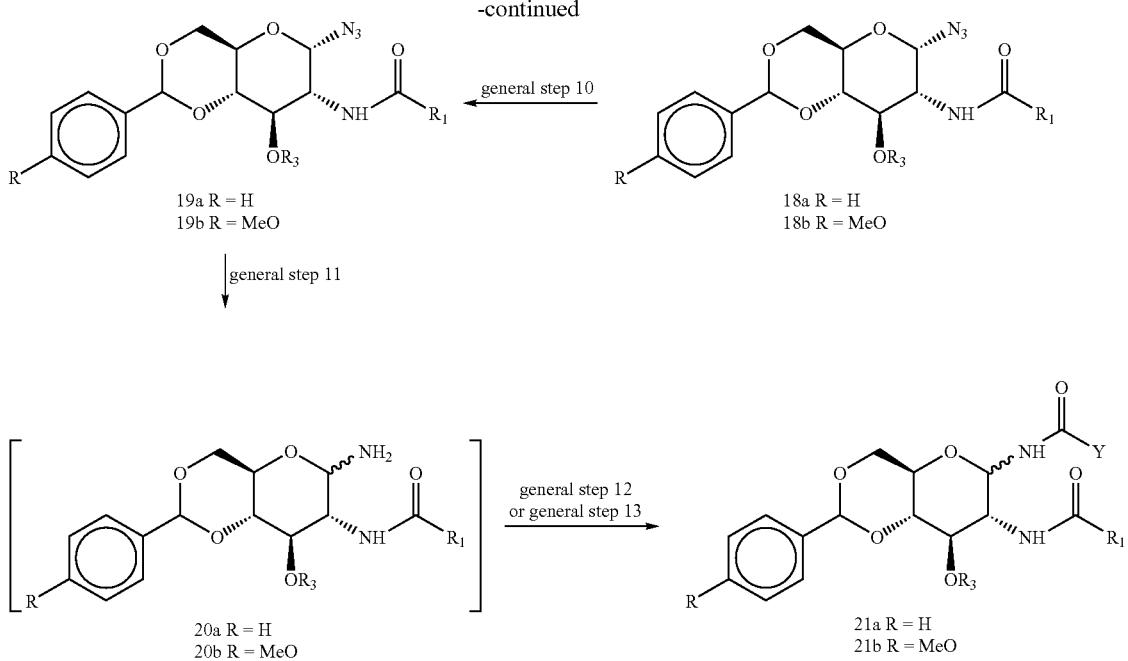
17 R₃=—CH₂CO₂Me
18 R₃=—CH₂CO₂H
19,20,21 R₃=—CH₂CONHOBn; —CH₂CONHCH(CH₃)CO₂Bn or 17, 18, 19, 20, 21 R₃=is 2-nitrophenyl; benzyl; 4-methylbenzyl; 4-chlorobenzyl; 4-methoxybenzyl; 4-phenylbenzyl; 1-naphthylmethyl; 2-naphthylinethyl.
R₁ is as defined in scheme 1+Dde; 4-methylphenyl.
Y is shown in the following list:
A
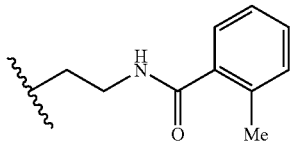
B
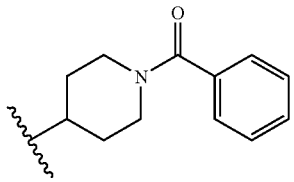
C
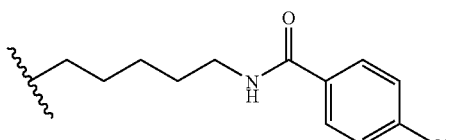
D
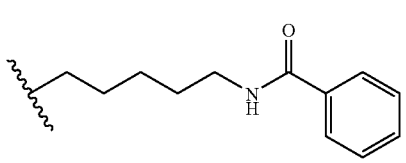
E
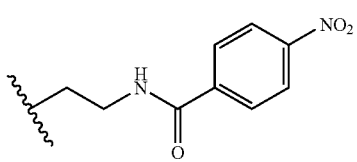
F
G
H
I J 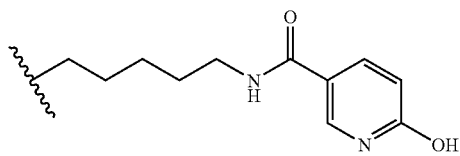

K 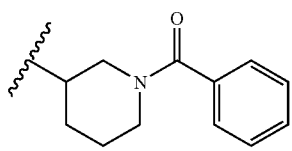

L 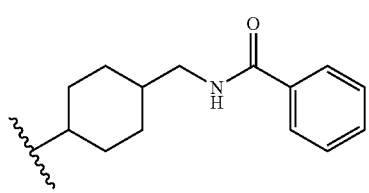

M 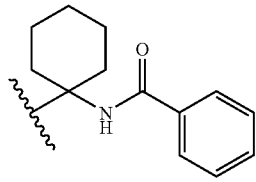

N 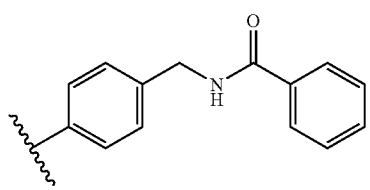

O 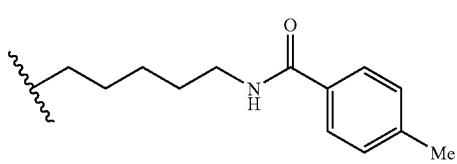

P 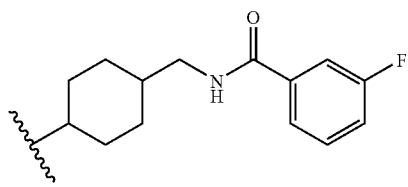

Q 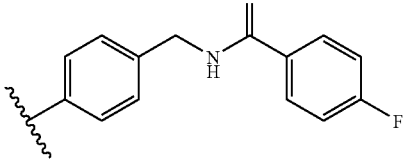

R 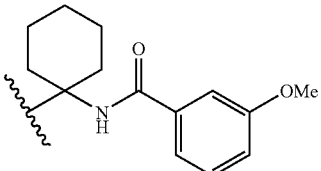

S 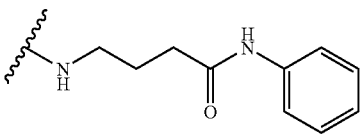

T 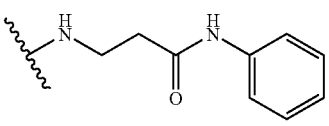

U 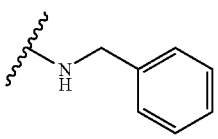

1-Deoxy-1-azido-3,4,6-tri-O-acetyl-2-deoxy-2-[1-(4, 4-dimethyl-2,6-dioxocyclohex-1-ylidene)-ethylariino]-α-D-glucopyranose (14):

3,4,6-tri-O-Acetyl-2-deoxy-2-[1-(4,4-dimethyl-2,6-dioxocyclohex-1-ylidene)-ethylamino]-α-D-glucopyranosyl bromide (3) (60 g, 0.112 mol) is suspended in acetonitrile (280 mL) and trimethylsilylazide (TMS-N$_3$) (29.9 mL, 0.224 mol) is added dropwise followed by the dropwise addition of tetrabutylammonium fluoride (1M TBAF in tetrahydrofuran) (225 mL, 0.225 mol). The reaction is stirred for 16 hr protected from light. The solvents are removed under reduced pressure, and the residue is preabsorbed on silica (150 g) and the product eluted with ethyl acetate/petroleum ether (1:1) (2 L). The solvents are evaporated and the crude residue used directly in the next step.

Alternative Preparation of 1-deoxy-1-azido-3,4,6-tri-O-acetyl-2-deoxy-2-[1-(4,4-dimethyl-2,6-dioxocyclohex-1-ylidene)-ethylamino]-α-D-glucopyranose (14):

3,4,6-tri-O-Acetyl-2-deoxy-2-[1-(4,4-dimethyl-2,6-dioxocyclohex-1-ylidene)-ethylamino]-α-D-glucopyranosyl bromide (3) (150 g, 0.282 mol) is suspended in ethyl acetate (3 L) and a solution of 10% aqueous sodium hydrogen carbonate (1500 mnL) containing sodium azide (22 g, 0.338 mol) is added. Tetrabutylammonium hydrogen sulfate (28.7 g, 30 mol %) was added and the biphasic mnixture stirred vigorously for 16 h. The organic layer was then separated, extracted and dried, then the solvent removed at reduced pressure. The residue was chromatographed as above to yield the desired product (105 g, 75%). $^1$H NMR (500 MHz, CDCl$_3$) δ 13.90 (d, J=9.6, 1H), 5.22 (t, J=9.6, 1H), 5.11 (t, J=9.7, 1H), 4.90 (d, J=8.9, 1H), 4.36 (dd, J=4.5, 12.5, 1H), 4.17 (dd, J=12.4, 1.7, 1H), 3.81-3.91 (m, 2H), 2.60 (s, 3H), 2.42 (s, 2H), 2.36 (s, 2H), 2.11, (s, 3H), 2.04 (s, 3H), 1.03 (s, 3H). m/z 495 (M+H).

1-Deoxy-1-azido-2-deoxy-2-amino-4,6-benzylidene-α-D-glucopyranose (15a):

The crude product 14 is taken up in methanol (450 m-L) and sodium metal (2.5 g, 0.112 mol) added carefully. The reaction vessel is guarded from the light and stirred for 45 minutes. The reaction is neutralized to pH 6 with Amberlite IR 120(H) resin. The resin is filtered and solvents evaporated under reduced pressure at rt. The residue is adsorbed on silica (150 g) and the product washed out with acetonitrile/water (1:1) (1 L). Solvents are evaporated under reduced pressure (at rt). Remaining water is removed by adding acetonitrile and evaporating under reduced pressure. The crude reaction product is suspended in acetonitrile (dry, 450 mL) and benzaldehyde dimnethyl acetale (34.3 g, 0.225 mol) and para-toluenesulfonic acid monohydrate (0.4 g, 0.225 mmol) were added. The reaction mixture is heated to 80° C. for 2 hours, then triethylamine (1 equivalent) added and solvents evaporated under reduced pressure. The residue is adsorbed on silica (150 g) and the silica washed with petroleum ether (500 mL). The product is eluted with ethyl acetate/petroleum ether (2/3). After evaporation of the solvents 42.73 g of crude product are obtained (83% yield from the bromo sugar 3). The product is then suspended in MeOH (475mL) and hydrazine hydrate (13.6 g, 0.25 mol) added at 0° C. The solution is stirred for 10 minutes and then another 90 minutes at rt. The volume is reduced under vacuum to half, ethyl acetate (200 tnL) is added and the organic solution washed with brine. The organic layer is dried on magnesium sulfate and evaporated to dryness. The residue is adsorbed on silica (100 g) and eluted with ethyl acetate/petroleum ether (3/2) (400 mL)then with ethyl acetate (400 nL) and finally with acetonitrile/ethyl acetate (1/5). The product is separated as a white solid (20.31 g, 74%). $^1$H NMR (500 MHz, CDCl$_3$) δ 7.32-7.53 (5H m aromatics), 5.54 (1H, S, Ph—C$\underline{H}$) 4.53 (1H, d, J-8.8, H-1), 4.3-4.4 (1H,m), 3.7-3.8 (1H, m), 3.4-3.6 (3H, m), 2.71 (1H, t,J=9, H-3), 1.62 (2H, br).

Cognate preparation of 1-Deoxy-1-azido-2-deoxy-2-amino-4,6-p-methoxybenzylidene-α-D-glucopyranose (15b):

This compound was prepared in an analogous manner to 15a except that 4-methoxy-benzaldehyde dimethyl acetal was used in place of benzaldehyde dimethyl acetal. $^1$H NMR (500 MHz, CDCl$_3$) δ 7.41 (d, J=10, 2H), 6.89 (d, J=10, 2H), 5.51 (1H, S) 4.54 (d, J=8.8,1H), 4.35 (dd, J=4.2, 10.5, 1H), 3.80 (s, 1H), 3.74-3.90 (m, 1H), 3.57-3.63 (m, 1H),3.50-3.55 (m, 2H), 2.71(1H, t, J=9.1, 1H.
m/z 323.18 (M+H).

General Step 5 to N-acylate 16a:
Example: 1-Deoxy-1-azido-2-deoxy-2-N-(acetyl)-amino-4,6-benzylidene-α-D-glucopyranose: the product is isolated in 97% yield (2.22 g, 6.6 mmol). $^1$H NMR (500 MHz, CDCl$_3$) δ 7.26-7.52 (5H, m, aromatics), 5.56 (1H, S, Ph—C$\underline{H}$), 4,83 (1H, d, J=9.3), 4.75 (1H, d, J=4.5), 4.3-4.4 (1H, m), 3.9-4 (1H, m), 3.7-3.8(1H, m), 3.6-3.7 (1H, m), 3.5-3.6 (2H, m), 2.0 (3H).

General Step 5 to N-acylate 16b:
Example: 1-Deoxy-1-azido-2-deoxy-2-N-(acetyl)-amino-4,6-p-methoxybenzylidene-α-D-glucopyranose was prepared by general method 5 utilising the symmetric anhydride (acetic anhydride).

$^1$H NMR (500 MHz, CDCl$_3$) δ 7.41 (d, J=8.5, 2H), 6.90 (d, J=7, 2H), 5.51 (1H, S) 5.01 (d,J=9.5,1H), 4.36 (dd, J=5, 10.5, 1H), 4.18 (t,J=10.0 1H), 3.81 (s, 3H), 3.78 (t,J=10.0 1H), 3.59 (dd, J=5, 9.5, 1H),3.54 (dd, J=9, 19, 1H), 3.46(dd, J=8.5, 18, 1H), 2.07 (s, 3H). m/z 365.3 (M+H).

Example: 1-Deoxy-1-azido-2-deoxy-2-N-(benzoyl)-amino-4,6-p-methoxybenzylidene-α-D-glucopyranose was prepared by general method 5 utilising the acid chloride (benzoyl chloride).

M/z 427.3 (M+H).

Example: 1-Deoxy-1-azido-2-deoxy-2-N-(tert-butylcarbonyl)-amino-4,6-p-methoxybenzylidene-α-D-glucopyranose was prepared by general method 5 utilising the acid chloride (2,2,2-trimethylacetyl chloride). M/z 407.4 (M+H).

General Step 6 to Prepare 17a:
Example: 1-Deoxy-1-azido-2-deoxy-2-N-(acetyl)-amino-4,6-benzylidene-3-(methyl acetate)-α-D-glucopyranose. Methyl bromoacetate was employed as the alkylating agent. The target product was isolated in 74% yield (1.97 g). $^1$H NMR (500 MHz, CDCl$_3$) δ 7.32-7.47 (5H, m, aromatics), 6.73 (1H, d, J=6.6), 5.55 (1H, s), 4.75 (1H, d, J=9.1), 4.3-4.5 (3H, m), 3.6-3.9 (7H,m), 3.5-3.6(1H, m), 2.1 (3H, s).

General Step 6 to Prepare 17b:
Example: 1-Deoxy-1-azido-2-deoxy-2-N-(acetyl)-amino-4,6-p-methoxybenzylidene-3-(methyl acetate)-α-D-glucopyranose: Methyl bromoacetate was employed as the alkylating agent. The target product was isolated in 85% yield. M/z 437.36 (M+H).

Example: 1-Deoxy-1-azido-2-deoxy-2-N-(benzoyl)-amino-4,6-p-methoxybenzylidene-3-(methyl acetate)-α-D-glucopyranose: Methyl bromoacetate was employed as the alkylating agent. The target product was isolated in 85% yield. M/z 499.4 (M+H).

Example: 1-Deoxy-1-azido-2-deoxy-2-N-(tert-butylacetyl)-amino-4,6-p-methoxybenzylidene-3-(methyl acetate)-α-D-glucopyranose: Methyl bromoacetate was employed as the alkylating agent. The target product was isolated in 85% yield. M/z 479.4 (M+H).

Example: Preparation of further C-3 alkylated compounds. The appropriate alkyl halide was employed in place of methyl bromoacetate as the alkylating agent. The target product was isolated and yields are shown in parentheses.

TABLE 4

MS data and yields for general step 6 Scheme 3 compounds 17b
Table of building blocks, MH+ values in ESMS and yields between brackets.

| $R_3 \downarrow \backslash R_1 \rightarrow$ | Dde | $CH_3$—CO | PhC(O)— | Ph-Ph-C(O)— |
|---|---|---|---|---|
| 2-NO$_2$-phenyl | 609 | 485 (61%) | 547 (40%) | 623 (68%) |
| benzyl | 577 | 455 (84%) | 517 (80%) | 593 (100%) |
| 4-Me-benzyl | 591 | 469 (51%) | 531 (55%) | 607 (63%) |
| 4-Cl-benzyl | 611 | 489 (87%) | 551 (89%) | 627 (97%) |
| 4-MeO-benzyl | 607 | 485 (50%) | 547 (80%) | 623 (95%) |
| 4-biphenyl-CH$_2$ | 653 | 531 (75%) | 593 (78%) | 669 (91%) |
| 1-naphthyl-CH$_2$ | 627 | 505 (80%) | 567 (86%) | 643 (100%) |
| 2-naphthyl-CH$_2$ | 627 | 505 (100%) | 567 (77%) | 643 (86%) |

General Step 10 to Prepare 19b: Where $R_3$ is other than —CH$_2$—COOMe, this Step is Omitted.

Example: The products of hydrolysis of 17b were coupled according to general step 10 with L-alanine-O-benzyl ester to yield compounds of general formula 19b. N-acetylated compound m/z 584.4 (M+H); N-benzoylated compound m/z 646.5 (M+H). In a cognate preparation, hydroxylamine-O-benzyl ether was coupled to the products of hydrolysis of 17b.

General Step 11: Reduction of the Azide with Pd/C or with Dithiol to Prepare 20a and 20b Method 1, with Pd/C: starting material (0.74 mmol) is dissolved in dichlorometdane (10 mL), catalyst (Pd/C, 150 mg) is added and the solution degassed. The reaction mixture is hydrogenated (H$_2$ at 1 atm) for 1 hour, then filtered and solvent evaporated under reduced pressure. The crude 1-amino glycoside is employed without further purification.

Example: 1-Deoxy-1-amino-2-deoxy-2-N-(acetyl)-amino-4,6-benzylidene-3-(methyl acetate)-α-D-glucopyranose: product was isolated in quantitative yield. $^1$H NMR (500 MHz, CDCl$_3$) δ 7.33-7.50 (5H, m, aromatics), 5.56 (1H, s), 4.47-4.55 (1H, m), 4.27-4.46 (2H, m), 4.15 (1H, d, J=9), 3.60-3.83 (7H,m), 3.37-3.44(1H, m), 2.08 (3H, s).

Method 2, with dithiol: starting material (0.12 mmol) is dissolved in chloroform/methanol (1/1) (1.2 mL), dithiotreitol (57 mg, 3 equiv) is added and the solution degassed using a nitrogen stream. The reaction mixture is stirred under nitrogen for 10 hours. The reaction mixture is diluted with chloroform, washed with water and brine, dried with magnesium sulfate and solvent evaporated. The crude 1-armno glycoside is employed without further purification for the generation for the isocyanate.

General Step 12: Formation of a Urea Bond 21a and 21b

The Y substituents are introduced by reacting of in situ generated isocyanate (from the 1-amino-pyranose 20a or 20b) with the amino functionality of the Y group.

The 1-isocyanato pyranose is first generated by treating the 1-aminopyranose 20 with one equivalent of one of the following reagents: phosgene, triphosgene, 1,1'-carbonyldiimidazole, or N,N'-disuccinimidyl carbonate. Suitable solvents for this purpose are dichloromethane, dimethylformamide or chloroform. The Y group is then added directly (1 equivalent) to the crude isocyanate mixture and the reaction is left stirring for 16 hours. 1 equivalent of diisopropylethylammne is added if the reaction is not complete after this time. The reaction is worked up by evaporating the solvents, adding dichloromethane and filtering the precipitated product.

The Y groups are prepared using commonly used amide bond forming procedures or urea bond forming procedures from commercially available precursors. Examples of suitable armide bond forming reagents include HBTU, BOP, HATU, and PyBOP. The urea bond in some of the Y groups are generated through the reaction of an isocyanate and an amine using well known procedures. The isocyanates are generated as above for the sugar isocyanate.

Y group reagents for general step 12 are in Table 5:

TABLE 5

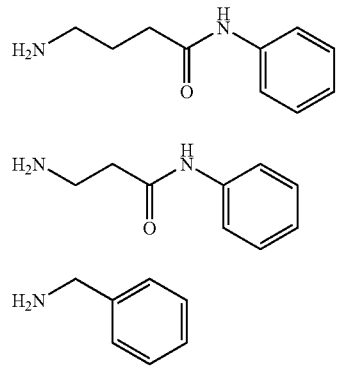

The compound where Y=benzylamine had m/z 514.52 M+H RT 8.55 minutes. $^1$H NMR: (CDCl$_2$) δ 1.83 (s, 3H) 3.45 (s, 3H) 3.30-4.30 (m 10H) 4.92 (dd, J=10Hz, 1Hz, 1H) 5.60 (s, 1H), 6.45 (d J=10Hz, 1H), 6.85 (t, J=6 Hz, 1H) 7.20-7.45 (m 10H), 8.20 (d J=9 Hz, 1H).

General Step 13: Formation of an Amide Bond 21a and 21b

The Y substituents are introduced through an amide bond formning reaction between the 1-aminopyranose 20 and the carboxylic acid functionality on the Y group. The amine 20 (0.2 mmol) is suspended in anhydrous DMF (1.2 mL) and a solution of the appropriate acid (0.95 equiv), HBTU (87 mg, 1.15 equiv), diisopropylamine (62 mg, 83 μL, 2.4 equiv) in DMF (0.8 mL) was added. The mixture was stirred for 16 hours and the solution then diluted with chloroform (10 mL), extracted with 10% citric acid solution, dried and solvents removed to yield the desired amides 21 in yields varying from 40% to 90%.

Y group reagents (carboxylic acids) for general step 13 are shown in table 6:

TABLE 6

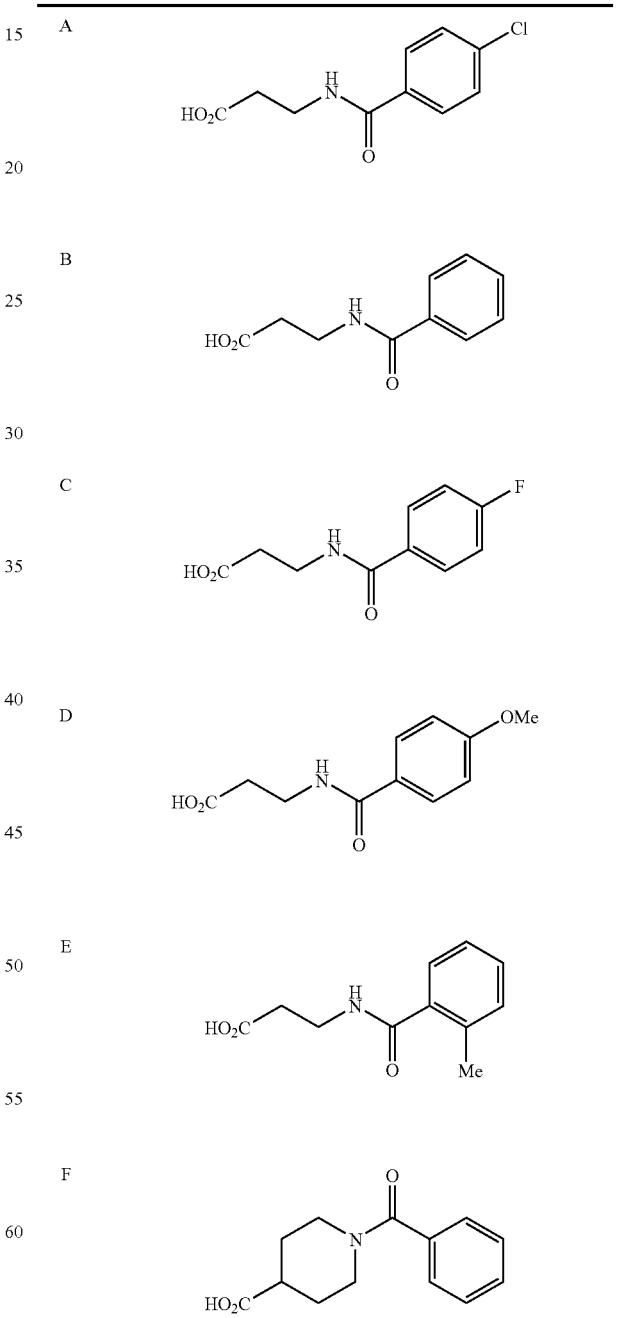

TABLE 6-continued
G 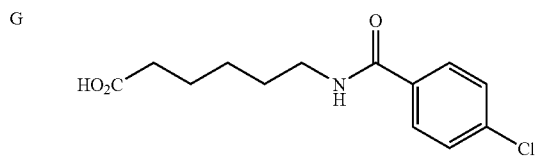
H 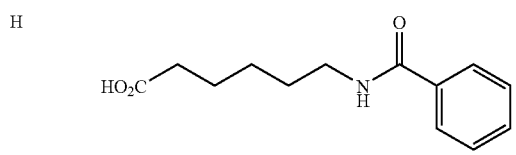
I 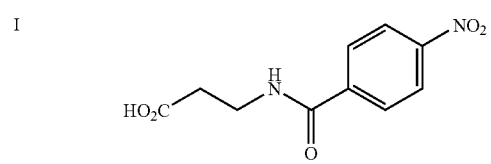
J 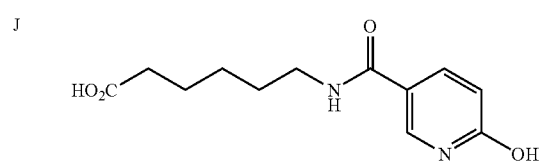
K 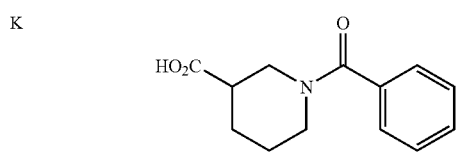
L 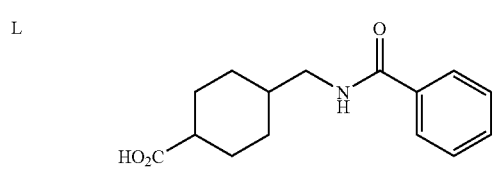
TABLE 6-continued
M 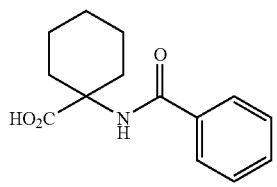
N 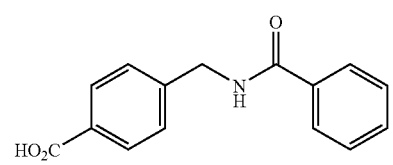
O 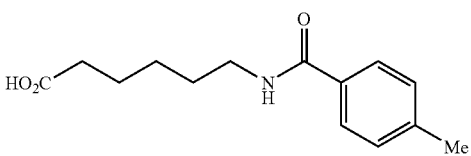
P 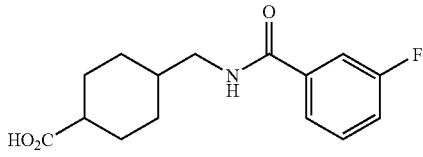
Q 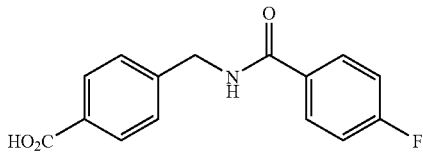
R 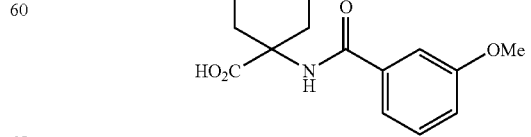

Scheme 4

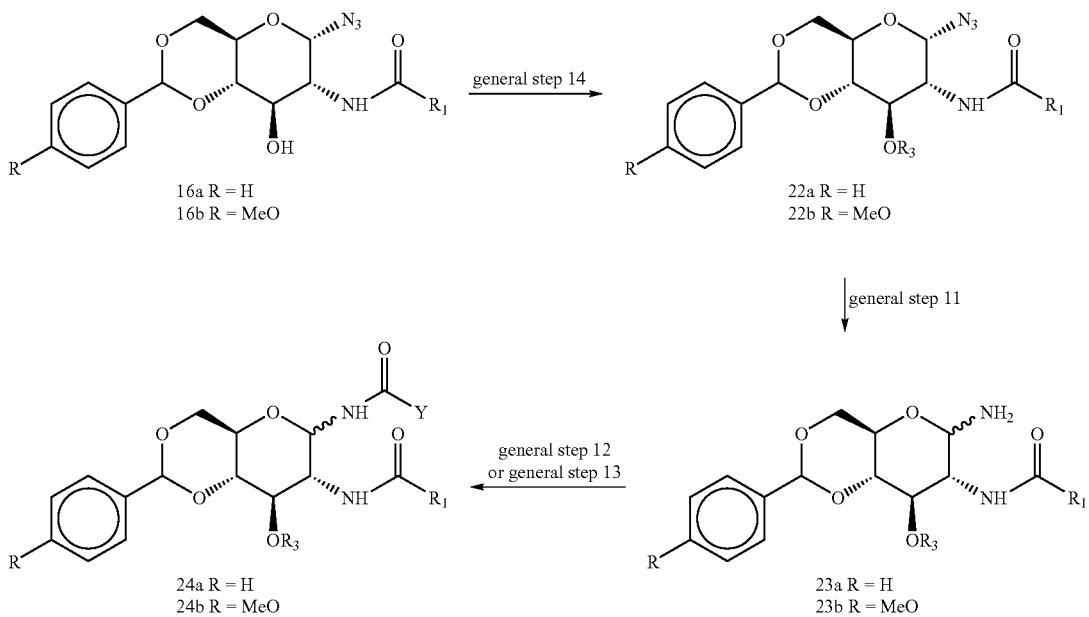

16a R = H
16b R = MeO

22a R = H
22b R = MeO

24a R = H
24b R = MeO

23a R = H
23b R = MeO $R^1$ is as defined in scheme 3
$R_3$ is acetyl; 4-chlorobenzoyl
Y is as is as defined in scheme 3

General Step 14. Acyl Protection of Compounds 16a and 16b to form 22a and 22b

Compound 16 (0.27 mrnol) was dissolved in DMF (1.4 mL) and diisopropylethylamnine (71 mg, 96 µL, 2 equiv) added. Acetic anhydride (56 mg, 52 µL, 2 equiv) was added followed by a catalytic amount of DMAP. The mixture was stirred for 16 h, water added and stirring continued for a further 30 nun. The mixture was diluted with chloroform, washed with 10% citric acid, $NaHCO_3$ solution, brine, dried ($MgSO_4$) and evaporated to give the desired compound as a white solid (85-95%).

In a cognate preparation 4-chlorobenzoyl chloride was used in place of acetic anhydride.

Example: 1-Deoxy-1-azido-2-deoxy-2-N-(acetyl)-amino-3-p-chlorobenzoyl-4,6-p-methoxybenzylidene-α-D-glucopyranose. $^1$H NMR (d6-DMSO, 500 MHz) δ 1.91 (s, 3 H), 3.71 (dt, J=7, 10 Hz, 1 H), 3.76 (s, 3 H), 3.84 (t, J=10 Hz, 1 H), 3.92 (t, J=9.5 Hz, 1 H), 4.12 (dd, J=9.5, 19 Hz, 1 H), 4.30 (dd, J=9.5, 10 Hz, 1 H), 5.07 (d, J=9.5 Hz, 1 H), 5.32 (t, J=10 Hz, 1 H), 5.63 (s, 1 H), 6.93 (d, J=8.5 Hz, 2 H), 7.32 (d, J=8.5 Hz, 2 H), 7.59 (d, J=8.5 Hz, 2 H), 7.78 (d, J=8.5 Hz, 2 H), 8.73 (d, J=9 Hz, 1 H)

Compounds of the type 21a, 21b, 24a and 24b were further elaborated by deprotection of ester groups as exemplified by general procedure 7 followed by cleavage of the benzylidene protecting groups according to general procedure 9 to yield the final compounds as exemplified by table 7. Compounds were analysed by HPLC/MS with evaporative light scattering detection. Retention times and peak purities for the peaks corresponding to the desired compound as detected by mass spectrometry are shown. NA denotes prepared but not analysed. Codes for Y are as shown in Table 6 above.

TABLE 7

| # | Y | $R_1$ | $R_3$ | Retention time | Purity % ELS (area) |
|---|---|---|---|---|---|
| 1 | B | Me | $CH_2CO_2Me$ | 1.82 | 77.7 |
| 2 | H | Me | $CH_2CO_2Me$ | 2.9 | 78.3 |
| 3 | G | Me | $CH_2CO_2Me$ | 3.4 | 51.2 |
| 4 | B | Ph | $CH_2CO_2Me$ | 3.35 | 49.1 |
| 5 | B | tert-Bu | $CH_2CO_2Me$ | 3.28 | 15.9 |
| 6 | B | Me | H | 1.25 | 66.0 |
| 7 | H | Me | H | 2.73 | 99.3 |
| 8 | A | tert-Bu | H | 3.51 | 82.1 |
| 9 | H | tert-Bu | H | 3.38 | 85.0 |
| 10 | G | tert-Bu | H | 3.75 | 86.4 |
| 11 | H | Me | $CH_2CO_2H$ | 2.92 | 80.9 |
| 12 | G | Me | $CH_2CO_2H$ | 3.43 | 83.0 |
| 13 | A | Ph | $CH_2CO_2H$ | 3.69 | 70.5 |
| 14 | H | Ph | $CH_2CO_2H$ | 3.6 | 88.9 |
| 15 | A | Me | $CH_2CO_2H$ | 3.06 | 87.9 |
| 16 | C | Me | $CH_2CO_2Me$ | 2.51 | 86.9 |
| 17 | F | Me | $CH_2CO_2Me$ | 2.65 | 86.5 |
| 18 | J | Me | $CH_2CO_2Me$ | 1.36 | 53.7 |
| 19 | D | Me | $CH_2CO_2Me$ | 2.57 | 83.2 |
| 20 | C | Ph | $CH_2CO_2Me$ | 3.46 | 92.9 |
| 21 | F | Ph | $CH_2CO_2Me$ | 3.45 | 51.8 |
| 22 | F | Ph | $CH_2CO_2Me$ | 3.69 | 45.1 |
| 23 | J | Ph | $CH_2CO_2Me$ | 2.99 | 69.1 |
| 24 | D | Ph | $CH_2CO_2Me$ | 3.41 | 73.6 |
| 25 | C | tert-Bu | $CH_2CO_2Me$ | 3.4 | 58.3 |
| 26 | F | tert-Bu | $CH_2CO_2Me$ | 3.38 | 55.5 |
| 27 | J | tert-Bu | $CH_2CO_2Me$ | 2.96 | 29.5 |
| 28 | D | tert-Bu | $CH_2CO_2Me$ | 3.35 | 62.3 |
| 29 | E | Me | $CH_2CO_2Me$ | 2.18 | 81.5 |
| 30 | E | Ph | $CH_2CO_2Me$ | 3.43 | 89.2 |
| 31 | E | tert-Bu | $CH_2CO_2Me$ | 3.34 | 23.4 |
| 32 | C | Me | H | 1.88 | 95.2 |
| 33 | F | Me | H | 2.19 | 95.1 |
| 34 | D | Me | H | 2.03 | 73.1 |
| 35 | F | Ph | H | 4.2 | 0.5 |
| 36 | C | tert-Bu | H | 3.23 | 89.0 |
| 37 | F | tert-Bu | H | 3.26 | 86.1 |
| 38 | J | tert-Bu | H | 2.64 | 85.3 |
| 39 | D | tert-Bu | H | 3.2 | 88.2 |
| 40 | E | Me | H | 1.5 | 95.0 |

TABLE 7-continued

| # | Y | R₁ | R₃ | Retention time | Purity % ELS (area) |
|---|---|---|---|---|---|
| 41 | E | tert-Bu | H | 3.17 | 90.5 |
| 42 | B | Me | CH₂CO₂H | 2.5 | 84.9 |
| 43 | J | Me | CH₂CO₂H | 0.91 | 72.3 |
| 44 | D | Me | CH₂CO₂H | 2.57 | 82.8 |
| 45 | C | Ph | CH₂CO₂H | 3.48 | 87.1 |
| 46 | F | Ph | CH₂CO₂H | 3.51 | 97.7 |
| 47 | J | Ph | CH₂CO₂H | 2.87 | 74.4 |
| 48 | D | Ph | CH₂CO₂H | 3.44 | 89.2 |
| 49 | C | tert-Bu | CH₂CO₂H | 3.41 | 96.0 |
| 50 | F | tert-Bu | CH₂CO₂H | 3.4 | 96.3 |
| 51 | J | tert-Bu | CH₂CO₂H | 2.83 | 38.1 |
| 52 | D | tert-Bu | CH₂CO₂H | 3.37 | 95.6 |
| 53 | E | Me | CH₂CO₂H | 2.22 | 83.0 |
| 54 | E | Ph | CH₂CO₂H | 3.43 | 83.1 |
| 55 | K | Me | CH₂CO₂Me | 2.88 | 33.2 |
| 56 | L | Me | CH₂CO₂Me | 3.07 | 37.1 |
| 57 | N | Me | CH₂CO₂Me | 3.16 | 54.0 |
| 58 | O | Me | CH₂CO₂Me | 3.26 | 66.2 |
| 59 | P | Me | CH₂CO₂Me | 3.26 | 61.4 |
| 60 | I | Me | CH₂CO₂Me | 2.74 | 55.9 |
| 61 | Q | Me | CH₂CO₂Me | 3.3 | 46.5 |
| 62 | K | Ph | CH₂CO₂Me | 3.61 | 90.4 |
| 63 | O | Ph | CH₂CO₂Me | 3.81 | 86.8 |
| 64 | I | Ph | CH₂CO₂Me | 3.52 | 87.1 |
| 65 | A | Me | CH₂CONHCH(CH₃)CO₂Bn | 4.09 | 85.8 |
| 66 | C | Me | CH₂CONHCH(CH₃)CO₂Bn | 3.93 | 88.6 |
| 67 | D | Me | CH₂CONHCH(CH₃)CO₂Bn | 3.95 | 89.1 |
| 68 | F | Me | CH₂CONHCH(CH₃)CO₂Bn | 3.89 | 86.0 |
| 69 | G | Me | CH₂CONHCH(CH₃)CO₂Bn | 4.38 | 85.4 |
| 70 | K | Me | CH₂CONHCH(CH₃)CO₂Bn | 3.93 | 86.3 |
| 71 | I | Me | CH₂CONHCH(CH₃)CO₂Bn | 3.98 | 80.2 |
| 72 | Q | Me | CH₂CONHCH(CH₃)CO₂Bn | 4.31 | 86.2 |
| 73 | Q | Ph | CH₂CO₂Me | 3.92 | 98.5 |
| 74 | A | pMePh | H | 4.00 | 30.7 |
| 75 | C | pMePh | H | 3.77 | 54.5 |
| 76 | F | pMePh | H | 3.75 | 64.0 |
| 77 | K | pMePh | H | 3.91 | 84.5 |
| 78 | M | pMePh | H | 4.85 | 2.1 |
| 79 | L | Me | CH₂CO₂H | 3.07 | 92.5 |
| 80 | N | Me | CH₂CO₂H | 3.15 | 59.9 |
| 81 | O | Me | CH₂CO₂H | 3.26 | 72.4 |
| 82 | P | Me | CH₂CO₂H | 3.25 | 69.4 |
| 83 | I | Me | CH₂CO₂H | 2.75 | 50.4 |
| 84 | Q | Me | CH₂CO₂H | 3.32 | 54.7 |
| 85 | R | Me | CH₂CO₂H | 4.32 | 79.2 |
| 86 | K | Ph | CH₂CO₂H | 3.61 | 80.7 |
| 87 | I | Ph | CH₂CO₂H | 3.53 | 88.2 |
| 88 | A | Me | CH₂CONHCH(CH₃)CO₂H | 2.66 | 18.5 |
| 89 | C | Me | CH₂CONHCH(CH₃)CO₂H | 2.87 | 69.4 |
| 90 | D | Me | CH₂CONHCH(CH₃)CO₂H | 2.60 | 1.7 |
| 91 | G | Me | CH₂CONHCH(CH₃)CO₂H | 3.50 | 51.8 |
| 92 | H | Me | CH₂CONHCH(CH₃)CO₂H | 3.07 | 81.0 |
| 93 | L | Me | CH₂CONHCH(CH₃)CO₂H | 3.17 | 52.5 |
| 94 | M | Me | CH₂CONHCH(CH₃)CO₂H | 3.34 | 83.7 |
| 95 | I | Me | CH₂CONHCH(CH₃)CO₂H | 2.97 | 64.3 |
| 96 | Q | Me | CH₂CONHCH(CH₃)CO₂H | 3.38 | 24.4 |
| 97 | C | Ph | CH₂CONHCH(CH₃)CO₂Bn | 4.58 | 93.0 |
| 98 | E | Ph | CH₂CONHCH(CH₃)CO₂Bn | 4.53 | 87.1 |
| 99 | F | Ph | CH₂CONHCH(CH₃)CO₂Bn | 4.49 | 91.8 |
| 100 | G | Ph | CH₂CONHCH(CH₃)CO₂Bn | 5.66 | 74.6 |
| 101 | H | Ph | CH₂CONHCH(CH₃)CO₂Bn | 4.71 | 87.2 |
| 102 | J | Ph | CH₂CONHCH(CH₃)CO₂Bn | 3.85 | 95.2 |
| 103 | K | Ph | CH₂CONHCH(CH₃)CO₂Bn | 4.65 & 4.78 | 74.4 |
| 104 | N | Ph | CH₂CONHCH(CH₃)CO₂Bn | 5.25 | 87.5 |
| 105 | P | Ph | CH₂CONHCH(CH₃)CO₂Bn | 5.35 | 55.8 |
| 106 | I | Ph | CH₂CONHCH(CH₃)CO₂Bn | 4.67 | 26.4 |
| 107 | Q | Ph | CH₂CONHCH(CH₃)CO₂Bn | 5.64 | 81.7 |
| 108 | B | Me | CH₂CONHOBn | 1.82 | 26.5 |
| 109 | C | Me | CH₂CONHOBn | 2.55 | 39.1 |
| 110 | D | Me | CH₂CONHOBn | 2.58 | 35.1 |
| 111 | B | Me | CH₂CONHOBn | 2.22 | 16.5 |
| 112 | F | Me | CH₂CONHOBn | 2.67 | 35.9 |
| 113 | G | Me | CH₂CONHOBn | 3.98 | 50.6 |
| 114 | H | Me | CH₂CONHOBn | 2.92 | 29.4 |
| 115 | J | Me | CH₂CONHOBn | 3.01 | 25.7 |
| 116 | N | Me | CH₂CONHOBn | 3.83 | 72.5 |
| 117 | A | Ph | CH₂CONHOBn | 3.70 | 66.2 |
| 118 | C | Ph | CH₂CONHOBn | 3.50 | 44.1 |
| 119 | D | Ph | CH₂CONHOBn | 4.01 | 50.8 |
| 120 | F | Ph | CH₂CONHOBn | 4.05 | 56.9 |
| 121 | G | Ph | CH₂CONHOBn | 3.92 | 80.1 |
| 122 | H | Ph | CH₂CONHOBn | 3.57 | 77.3 |
| 123 | K | Ph | CH₂CONHOBn | 3.60 | 48.4 |
| 124 | L | Ph | CH₂CONHOBn | 3.71 | 72.5 |
| 125 | P | Ph | CH₂CONHOBn | 3.84 | 77.4 |
| 126 | Q | Ph | CH₂CONHOBn | 3.91 | 57.8 |
| 127 | A | Ph | CH₂CONHCH(CH₃)CO₂H | 3.72 | 36.6 |
| 128 | E | Ph | CH₂CONHCH(CH₃)CO₂H | 3.47 | 87.2 |
| 129 | F | Ph | CH₂CONHCH(CH₃)CO₂H | 3.48 | 92.4 |
| 130 | G | Ph | CH₂CONHCH(CH₃)CO₂H | 0.00 | 0.0 |
| 131 | H | Ph | CH₂CONHCH(CH₃)CO₂H | 3.61 | 92.1 |
| 132 | J | Ph | CH₂CONHCH(CH₃)CO₂H | 2.90 | 91.4 |
| 133 | K | Ph | CH₂CONHCH(CH₃)CO₂H | 4.65 & 4.80 | 74.7 |
| 134 | L | Ph | CH₂CONHCH(CH₃)CO₂H | 3.70 | 93.9 |
| 135 | N | Ph | CH₂CONHCH(CH₃)CO₂H | 3.77 | 94.8 |
| 136 | P | Ph | CH₂CONHCH(CH₃)CO₂H | 3.84 | 87.3 |
| 137 | I | Ph | CH₂CONHCH(CH₃)CO₂H | 3.53 | 55.0 |
| 138 | B | tert-Bu | CH₂CO₂H | NA | NA |
| 139 | A | tert-Bu | CH₂CO₂H | NA | NA |
| 140 | H | tert-Bu | CH₂CO₂H | NA | NA |
| 141 | F | Me | CH₂CO₂H | NA | NA |
| 142 | M | Me | CH₂CO₂Me | NA | NA |
| 143 | R | Me | CH₂CO₂Me | NA | NA |
| 144 | H | Me | CH₂CONHCH(CH₃)CO₂Bn | NA | NA |
| 145 | L | Me | CH₂CONHCH(CH₃)CO₂Bn | NA | NA |
| 146 | P | Me | CH₂CONHCH(CH₃)CO₂Bn | NA | NA |
| 147 | J | pClPh | H | NA | NA |
| 148 | R | pClPh | H | NA | NA |
| 149 | D | pMePh | H | NA | NA |
| 150 | H | pMePh | H | NA | NA |
| 151 | P | pMePh | H | NA | NA |
| 152 | I | pMePh | H | NA | NA |
| 153 | Q | pMePh | H | NA | NA |
| 154 | K | Me | CH₂CO₂H | NA | NA |
| 155 | M | Me | CH₂CO₂H | NA | NA |
| 156 | L | Ph | CH₂CONHCH(CH₃)CO₂Bn | NA | NA |
| 157 | M | Ph | CH₂CONHCH(CH₃)CO₂Bn | NA | NA |
| 158 | B | Ph | H | NA | NA |
| 159 | H | Ph | H | NA | NA |
| 160 | G | Ph | H | NA | NA |
| 161 | C | Ph | H | NA | NA |
| 162 | E | Ph | H | NA | NA |
| 163 | D | Ph | H | NA | NA |
| 164 | A | Ph | H | NA | NA |
| 165 | B | Ph | H | NA | NA |
| 166 | H | Ph | H | NA | NA |
| 167 | G | Ph | H | NA | NA |
| 168 | C | Ph | H | NA | NA |
| 169 | E | Ph | H | NA | NA |
| 170 | D | Ph | H | NA | NA |
| 171 | A | Ph | H | NA | NA |
| 172 | K | pClPh | H | NA | NA |
| 173 | O | pClPh | H | NA | NA |
| 174 | I | pClPh | H | NA | NA |
| 175 | B | pClPh | H | NA | NA |
| 176 | H | pClPh | H | NA | NA |
| 177 | G | pClPh | H | NA | NA |
| 178 | C | pClPh | H | NA | NA |
| 179 | F | pClPh | H | NA | NA |
| 180 | E | pClPh | H | NA | NA |
| 181 | D | pClPh | H | NA | NA |
| 182 | A | pClPh | H | NA | NA |
| 183 | K | pClPh | H | NA | NA |
| 184 | O | pClPh | H | NA | NA |
| 185 | I | pClPh | H | NA | NA |
| 186 | B | pClPh | H | NA | NA |
| 187 | H | pClPh | H | NA | NA |
| 188 | G | pClPh | H | NA | NA |

TABLE 7-continued

| # | Y | $R_1$ | $R_3$ | Retention time | Purity % ELS (area) |
|---|---|---|---|---|---|
| 189 | C | pClPh | H | NA | NA |
| 190 | F | pClPh | H | NA | NA |
| 191 | E | pClPh | H | NA | NA |
| 192 | D | pClPh | H | NA | NA |
| 193 | A | pClPh | H | NA | NA |
| 194 | L | pMePh | H | NA | NA |
| 195 | O | pMePh | H | NA | NA |
| 196 | R | pMePh | H | NA | NA |
| 197 | B | pMePh | H | NA | NA |
| 198 | G | pMePh | H | NA | NA |
| 199 | E | pMePh | H | NA | NA |
| 200 | L | pMePh | H | NA | NA |
| 201 | O | pMePh | H | NA | NA |
| 202 | R | pMePh | H | NA | NA |
| 203 | B | pMePh | H | NA | NA |
| 204 | G | pMePh | H | NA | NA |
| 205 | E | pMePh | H | NA | NA |

Preparation of Sulfonamide Derivative 25

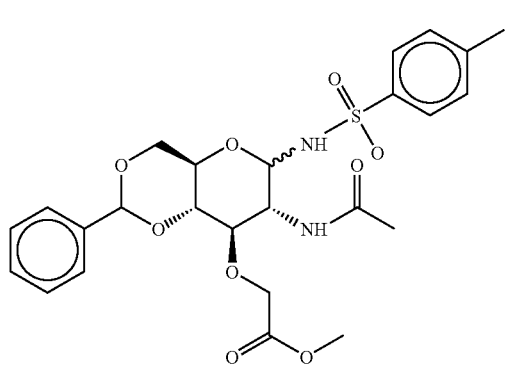

Compound 19a (40 mg) in which $R_1$ is methyl and $R_3$ is —CH$_2$COOMe was dissolved in dichloromethane (1 mL), to which was added triethylamine (13 mg, 1.2 equiv) followed by p-toluenesulfonyl chloride (24 mg, 1.2 equiv). The reaction was stirred at room temperature for 18 hours, diluted with dichloromethane and extracted with 100% citric acid, saturated sodium hydrogen carbonate and brine, dried over magnesium sulfate and the solvents removed in vacuo to yield 25 (33 mg, 59%).

Solid Phase Approach

The groups may be attached to a solid support via an ester linking bond ($R_6$ or $R_9$=resin-CH$_2$—CO—). These resin bound groups are prepared by linking α-amino, α-hydroxy, or α-mercapto acids to a commercially available hydroxy or chloromethylated resin. Suitable examples include but are not limiteds to tentagel-OH, hydroxymethyl polystyrene, Novasyn TG-hydroxy resin, or chloromethylated polystyrene.

Exemplary compounds were synthesized on solid support as described by the following reaction scheme 5:

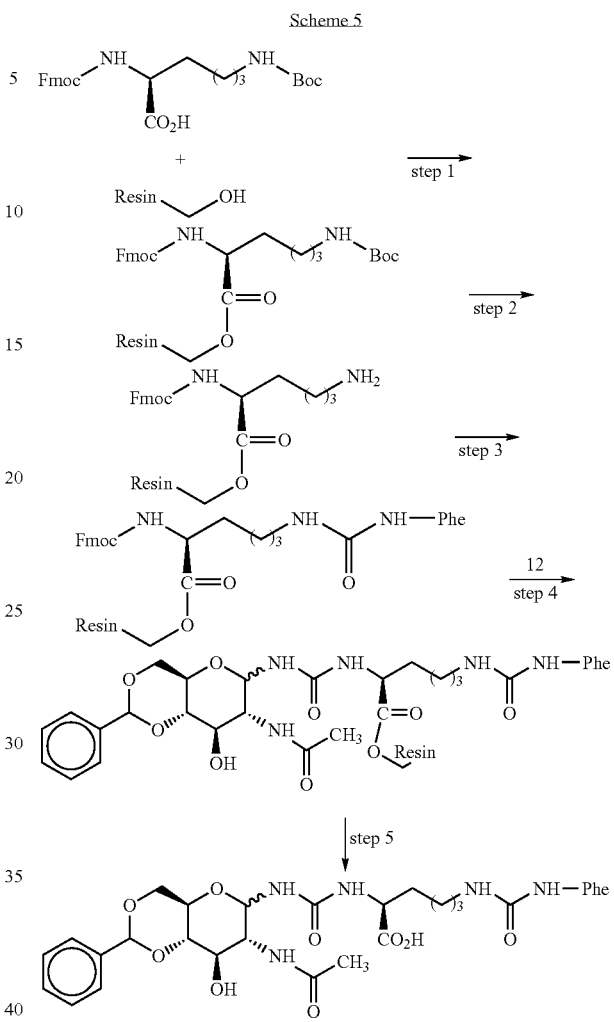

Solid Phase Step 1: Attachment to Hydroxy-resin

Novasyn TG-hydroxy resin (purchased from Novabiochem) (1 g, 0.37 mmol/g) is mixed with DMF (6 mL), left standing for 30 min. and then filtered off Fmoc-L-Lysine (Boc)-OH (940 mg, 2 mmol) is dissolved in dichloromethane (4 mL) at 0° C. and dicyclohexylcarbodiimide (206 mg, 1 mmol) is added at once. After 20 minutes the DCM is evaporated, DMF (3 mL) added and the solution is added to the filtered resin. Dimethylaminopyridine (5 mg, 0.04 mmol) is added to the mixture and the reaction is left for 60 minutes. The resin is filtered and washed with DMF (3×6 mL), MeOH/DCM (1:1) (3×6mL), and finally DCM (3×6 mL). The resin is further dried by air.

Solid Phase Step 2: Removal of the Boc Group

The resin (1.1 g) is treated with a solution of trifluoroacetic acid (3 mL) in DCM (3 mL) for 2 minutes. The resin is then filtered and washed with DCM (5×6mL).

Solid Phase Step 3

DCM (6 mL) is added to the resin (1.1 g), followed by diisopropylethylamine (0.65 mL, 3.7 mmol) and triphosgene (90 mg, 0.25 mmol). After 10 minutes the solvent is filtered and the resin washed with DCM (3×6 mL). Aniline (186 mg, 2 mmol) is dissolved in DCM (4 mL) and the solution added to the resin. After 30 minutes the resin is filtered, washed with DCM (4×4mL) and air dried.

Solid Phase Step 4

The resin (1.1 g) is treated with piperidine/DMF (1:1) (5 mL) for 5 minutes. The resin is filtered and washed with DMF (3×6 mL), MeOH/DCM (1:1) (3×6mL), and finally DCM (3×6mL). DCM (6 mL) is added to the resin followed by diisopropylethylarnmine (0.65 mL, 3.7 mmol) and triphosgene (90 mg, 0.25 mmol). After 10 minutes the solvent is filtered and the resin washed with DCM (3×6 mL). 4,6-Benzylidene-2-deoxy-2-N-acetamnido-1-deoxy-1-amino-alpha-D-muramic acid (155 mg, 0.4 mmol) is dissolved in DMF (4 mL) and the solution added to the resin. After 12 hours the resin is filtered and washed with DMF (3×6 mL), MeOH/DCM (1:1) (3×6mL), and finally DCM (3×6 mL). The resin is further dried by air.

Solid Phase Step 5

A solution of aqueous NaOH (1M, 0.2 mL) and MeOH (2mL) is added to the resin and the reaction left for 40 min. The resin is filtered and washed with MeOH (3×6mL). The filtrates are combined, neutralized with 0.1M HCl and solvent evaporated. The target product was detected by LCMS at m/z 658 (M+H), Molecular Weight calc. For $C_{31}H_{39}N_5O_{11}$: 657 g/mol.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

We claim:

1. A compound of the formula:

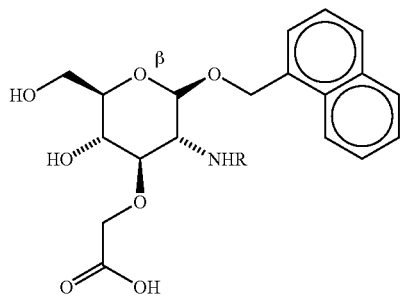

wherein R is selected from the group consisting of acetyl, benzoyl, biphenylcarbonyl and tert-butylcarbonyl.

2. A compound of the formula:

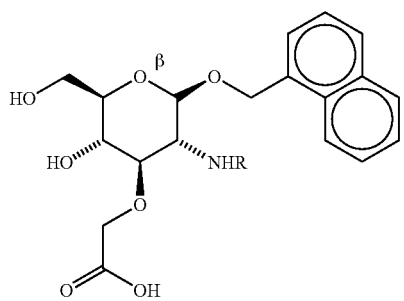

wherein R is acetyl.

3. A compound of the formula:

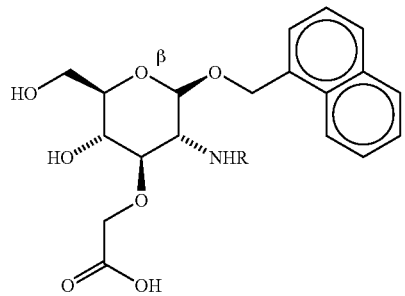

wherein R is benzoyl.

4. A compound of the formula:

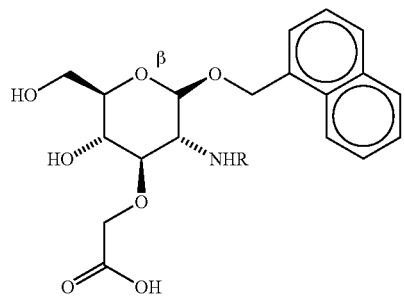

wherein R is biphenylcarbonyl.

5. A compound of the formula:

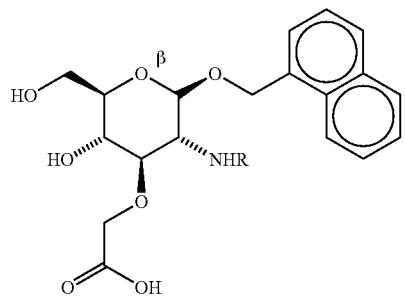

wherein R is tert-butylcarbonyl.

6. A library of compounds, comprising a plurality of compounds as defined in claim 1.

* * * * *